United States Patent
Lord et al.

(10) Patent No.: US 10,357,384 B2
(45) Date of Patent: *Jul. 23, 2019

(54) RADIALLY EXPANDABLE POLYMER PROSTHESIS AND METHOD OF MAKING SAME

(71) Applicant: Abbott Cardiovascular Systems Inc., Santa Clara, CA (US)

(72) Inventors: Brenna Hearn Lord, Palo Alto, CA (US); Nicole F. Perzov, San Carlos, CA (US); Timothy A. Limon, Cupertino, CA (US)

(73) Assignee: ABBOTT CARDIOVASCULAR SYSTEM INC., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/754,360

(22) Filed: Jun. 29, 2015

(65) Prior Publication Data

US 2015/0297372 A1    Oct. 22, 2015

Related U.S. Application Data

(60) Continuation of application No. 13/665,529, filed on Oct. 31, 2012, now Pat. No. 9,079,354, which is a
(Continued)

(51) Int. Cl.
*A61F 2/86* (2013.01)
*A61F 2/89* (2013.01)
(Continued)

(52) U.S. Cl.
CPC .............. *A61F 2/82* (2013.01); *A61F 2/91* (2013.01); *A61F 2/915* (2013.01); *A61L 31/06* (2013.01);
(Continued)

(58) Field of Classification Search
CPC .......... A61F 2240/00; A61F 2/82; A61F 2/89; A61F 2/06; A61F 2/07; A61F 2/86;
(Continued)

(56) References Cited

U.S. PATENT DOCUMENTS 5,514,154 A * 5/1996 Lau ........................... A61F 2/86
                                                      606/108
5,911,732 A * 6/1999 Hojeibane ............... A61F 2/915
                                                      606/194

(Continued)

*Primary Examiner* — Seema Mathew
(74) *Attorney, Agent, or Firm* — Squire Patton Boggs (US) LLP

(57) ABSTRACT

Polymeric stents having fracture toughness and resistance to recoil after deployment are disclosed along with methods of manufacturing such stents. Improvements to mechanical characteristics and other improvements may be achieved by having polymer chains within individual stent struts oriented in a direction that is closer to or in line with the axis of the individual stent struts. The struts are connected to each other by hinge elements that are configured to bend during crimping and deployment of the stent. Ring struts form ring structures. A ring structure can have an overall curvilinear length from about 12 mm to about 15 mm.

10 Claims, 12 Drawing Sheets

Related U.S. Application Data division of application No. 12/831,440, filed on Jul. 7, 2010, now Pat. No. 8,303,644, which is a continuation-in-part of application No. 12/114,608, filed on May 2, 2008, now Pat. No. 8,002,817.

(60) Provisional application No. 61/323,789, filed on Apr. 13, 2010, provisional application No. 60/927,785, filed on May 4, 2007.

(51) Int. Cl.
| | | |
|---|---|---|
| *A61F 2/82* | (2013.01) | |
| *A61F 2/91* | (2013.01) | |
| *A61F 2/915* | (2013.01) | |
| *B29C 67/00* | (2017.01) | |
| *A61L 31/06* | (2006.01) | |
| *B26D 3/10* | (2006.01) | |
| *B26D 7/14* | (2006.01) | |
| *A61F 2/00* | (2006.01) | |
| *B29C 53/02* | (2006.01) | |
| *B29C 55/24* | (2006.01) | |
| *B29L 31/00* | (2006.01) | |

(52) U.S. Cl.
CPC .............. *B26D 3/10* (2013.01); *B26D 7/14* (2013.01); *B29C 67/0014* (2013.01); *A61F 2/0077* (2013.01); *A61F 2002/91558* (2013.01); *A61F 2002/91566* (2013.01); *A61F 2002/91575* (2013.01); *A61F 2210/0004* (2013.01); *A61F 2230/0069* (2013.01); *A61F 2250/0067* (2013.01); *B29C 53/02* (2013.01); *B29C 55/24* (2013.01); *B29C 2793/0009* (2013.01); *B29L 2031/7534* (2013.01); *Y10T 29/49826* (2015.01); *Y10T 29/49925* (2015.01); *Y10T 83/0424* (2015.04); *Y10T 156/1043* (2015.01)

(58) Field of Classification Search
CPC ............ A61F 2002/91566; A61F 2/915; A61F 2002/91533; A61F 2002/825; B23K 2201/06; B23K 2203/00; B23K 2203/42; B23K 26/38; B23K 26/402
See application file for complete search history.

(56) References Cited

U.S. PATENT DOCUMENTS

| | | | | |
|---|---|---|---|---|
| 5,928,280 | A * | 7/1999 | Hansen | A61F 2/86 600/36 |
| 6,283,990 | B1 * | 9/2001 | Kanesaka | A61F 2/86 623/1.11 |
| 6,635,083 | B1 * | 10/2003 | Cheng | A61F 2/91 623/1.15 |
| 7,691,461 | B1 * | 4/2010 | Prabhu | A61F 2/82 428/36.9 |
| 7,704,274 | B2 * | 4/2010 | Boyle | A61F 2/07 623/1.13 |
| 7,763,066 | B2 * | 7/2010 | Parker | A61F 2/91 606/200 |
| 7,824,441 | B2 * | 11/2010 | Santos | A61F 2/91 623/1.42 |
| 7,959,665 | B2 * | 6/2011 | Pienknagura | A61F 2/91 623/1.16 |
| 8,206,436 | B2 * | 6/2012 | Mangiardi | A61F 2/07 623/1.46 |
| 8,876,888 | B2 * | 11/2014 | Lee | A61F 2/91 623/1.15 |
| 2003/0033003 | A1 * | 2/2003 | Harrison | A61F 2/91 623/1.15 |
| 2007/0293938 | A1 * | 12/2007 | Gale | A61F 2/91 623/1.15 |
| 2008/0275537 | A1 * | 11/2008 | Limon | A61F 2/91 623/1.15 |
| 2011/0190871 | A1 * | 8/2011 | Trollsas | A61F 2/91 623/1.15 |
| 2011/0270383 | A1 * | 11/2011 | Jow | A61F 2/915 623/1.16 |
| 2011/0270384 | A1 * | 11/2011 | Lord | A61F 2/82 623/1.16 |
| 2012/0143307 | A1 * | 6/2012 | Dreher | A61F 2/91 623/1.15 |
| 2012/0271396 | A1 * | 10/2012 | Zheng | A61F 2/82 623/1.2 |
| 2013/0085564 | A1 * | 4/2013 | Papp | A61F 2/915 623/1.15 |
| 2015/0374521 | A1 * | 12/2015 | Zheng | A61F 2/915 623/1.2 |
| 2016/0081824 | A1 * | 3/2016 | Harrington | B23K 26/38 29/517 |
| 2016/0213499 | A1 * | 7/2016 | Zheng | A61F 2/915 |

* cited by examiner

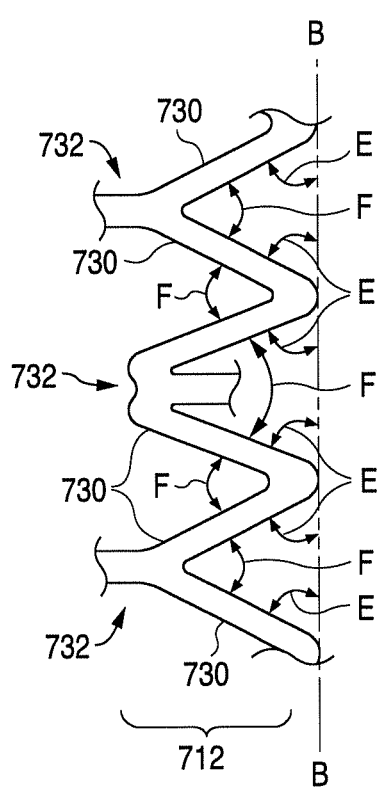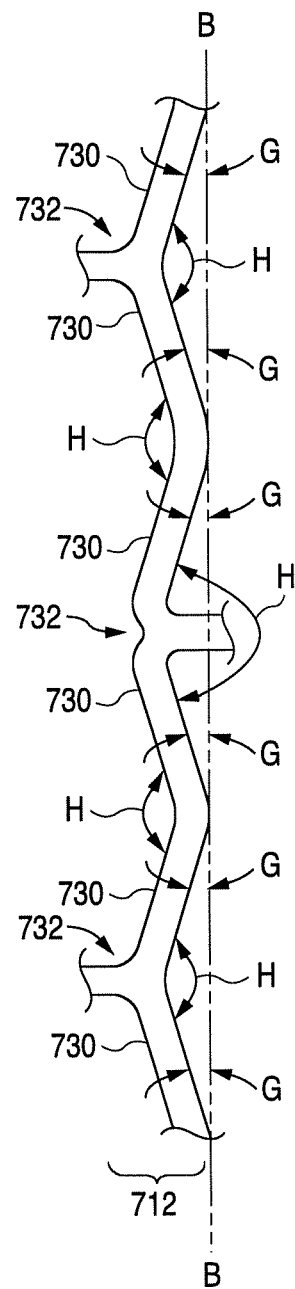
FIG. 7  FIG. 8

CL=4.0 mm, expanded to ID=3.5mm

CL=4.5 mm, expanded to ID~3.5mm

CL>4.5 mm, expanded to ID=3.5mm

CL=4.0 mm, crimped

CL=4.5 mm, crimped

CL>4.5 mm, crimped

RADIALLY EXPANDABLE POLYMER PROSTHESIS AND METHOD OF MAKING SAME

CROSS-REFERENCE TO RELATED APPLICATIONS

This application is a continuation of application Ser. No. 13/665,529, filed Oct. 31, 2012, now U.S. Pat. No. 9,079,354, which is a divisional of application Ser. No. 12/831,440, filed Jul. 7, 2010, now U.S. Pat. No. 8,303,644, which claims the benefit of Provisional Application No. 61/323,789, filed Apr. 13, 2010 and is a continuation-in-part of application Ser. No. 12/114,608, filed May 2, 2008, now U.S. Pat. No. 8,002,817, which claims the benefit of Provisional Application No. 60/927,785, filed May 4, 2007, all of which applications are incorporated herein by reference.

FIELD OF THE INVENTION

This invention relates to expandable endoprostheses, and more particularly to polymeric stents and methods of manufacturing polymeric stents.

BACKGROUND OF THE INVENTION

An "endoprosthesis" corresponds to an artificial device that is placed inside the body, more particularly, within an anatomical lumen. A "lumen" refers to a cavity of a tubular organ such as a blood vessel.

A stent is an example of such an endoprosthesis. Stents are generally cylindrically shaped devices, which function to hold open and sometimes expand a segment of a blood vessel or other anatomical lumen such as urinary tracts and bile ducts. Stents are often used in the treatment of atherosclerotic stenosis in blood vessels. "Stenosis" refers to a narrowing or constriction of the diameter of a bodily passage or orifice. In such treatments, stents reinforce body vessels and prevent restenosis following angioplasty in the vascular system. "Restenosis" refers to the reoccurrence of stenosis in a blood vessel or heart valve after it has been treated (as by balloon angioplasty, stenting, or valvuloplasty) with apparent success. The treatment of a diseased site or lesion with a stent involves both delivery and deployment of the stent. "Delivery" refers to introducing and transporting the stent through a bodily lumen to a region, such as a lesion, in a vessel that requires treatment. "Deployment" corresponds to the expanding of the stent within the lumen at the treatment region. Delivery and deployment of a stent are accomplished by positioning the stent about one end of a catheter, inserting the end of the catheter through the skin into a bodily lumen, advancing the catheter in the bodily lumen to a desired treatment location, expanding the stent at the treatment location, and removing the catheter from the lumen.

In the case of a balloon expandable stent, the stent is mounted about a balloon disposed on the catheter. Mounting the stent typically involves compressing or crimping the stent onto the balloon. The stent is then expanded by inflating the balloon. The balloon may then be deflated and the catheter withdrawn. In the case of a self-expanding stent, the stent may be secured to the catheter via a retractable sheath or a sock. When the stent is in a desired bodily location, the sheath may be withdrawn which allows the stent to self-expand.

The stent must be able to satisfy a number of mechanical requirements. First, the stent must be capable of withstanding the structural loads, namely radial compressive forces, imposed on the stent as it supports the walls of a vessel. Therefore, a stent must possess adequate radial strength. Radial strength, which is the ability of a stent to resist radial compressive forces, is due to strength and rigidity around a circumferential direction of the stent. Radial strength and rigidity, therefore, may also be described as, hoop or circumferential strength and rigidity.

Once expanded, the stent must adequately maintain its size and shape throughout its service life despite the various forces that may come to bear on it, including the cyclic loading induced by the beating heart. For example, a radially directed force may tend to cause a stent to recoil inward. Generally, it is desirable to minimize recoil.

In addition, the stent must possess sufficient flexibility to allow for crimping, expansion, and cyclic loading. Longitudinal flexibility is important to allow the stent to be maneuvered through a tortuous vascular path and to enable it to conform to a deployment site that may not be linear or may be subject to flexure. Finally, the stent must be biocompatible so as not to trigger any adverse vascular responses.

The structure of a stent is typically composed of scaffolding that includes a pattern or network of interconnecting structural elements often referred to in the art as struts or bar arms. The scaffolding can be formed from wires, tubes, or sheets of material rolled into a cylindrical shape. The scaffolding is designed so that the stent can be radially compressed (to allow crimping) and radially expanded (to allow deployment). A conventional stent is allowed to expand and contract through movement of individual structural elements with respect to each other.

Additionally, a medicated stent may be fabricated by coating the surface of either a metallic or polymeric scaffolding with a polymeric carrier that includes an active or bioactive agent or drug. Polymeric scaffolding may also serve as a carrier of an active agent or drug.

Furthermore, it may be desirable for a stent to be biodegradable. In many treatment applications, the presence of a stent in a body may be necessary for a limited period of time until its intended function of, for example, maintaining vascular patency and/or drug delivery is accomplished. Therefore, stents fabricated from biodegradable, bioabsorbable, and/or bioerodable materials such as bioabsorbable polymers should be configured to completely erode only after the clinical need for them has ended.

However, there are potential shortcomings in the use of polymers as a material for implantable medical devices, such as stents. There is a need for a manufacturing process for a stent that addresses such shortcomings so that a polymeric stent can meet the clinical and mechanical requirements of a stent.

Polymers have been used to make stent scaffolding. The art recognizes a variety of factors that affect a polymeric stent's ability to retain its structural integrity when subjected to external loadings, such as crimping and balloon expansion forces. These interactions are complex and the mechanisms of action not fully understood. According to the art, characteristics differentiating a polymeric, bio-absorbable stent scaffolding of the type expanded to a deployed state by plastic deformation from a similarly functioning metal stent are many and significant. Indeed, several of the accepted analytic or empirical methods/models used to predict the behavior of metallic stents tend to be unreliable, if not inappropriate, as methods/models for reliably and consistently predicting the highly non-linear behavior of a polymeric load-bearing, or scaffolding portion of a balloon-expandable stent. The models are not generally capable of providing an acceptable degree of certainty required for purposes of implanting the stent within a body, or predicting/ anticipating the empirical data.

Polymer material considered for use as a polymeric stent scaffolding, such as PLLA and PLGA, may be described through comparison with a metallic material conventionally used to form stent scaffolding. In comparison to metals, a suitable polymer has a low strength to weight ratio, which means more material is needed to provide an equivalent mechanical property to that of a metal. Therefore, struts in polymeric scaffolding must be made thicker and wider to have the strength needed. Polymeric scaffolding also tends to be brittle or have limited fracture toughness. The anisotropic and rate-dependant inelastic properties (i.e., strength/ stiffness of the material varies depending upon the rate at which the material is deformed) that are inherent in the material only compound this complexity in working with a polymer, particularly, a bio-absorbable polymer such as PLLA and PLGA.

Therefore, processing steps performed on and design changes made to a metal stent that have not typically raised concerns for unanticipated changes in the average mechanical properties, may not also apply to a polymer stent due to the non-linear and sometimes unpredictable nature of the mechanical properties of the polymer under a similar loading condition. It is sometimes the case that one needs to undertake extensive validation before it even becomes possible to predict more generally whether a particular condition is due to one factor or another—e.g., was a defect the result of one or more steps of a fabrication process, or one or more steps in a process that takes place after stent fabrication, e.g., crimping. As a consequence, a change to a fabrication process, post-fabrication process or even relatively minor changes to a stent pattern design must, generally speaking, be investigated more thoroughly than if a metallic material were used instead of the polymer. It follows, therefore, that when choosing among different polymeric stent designs for improvement thereof, there are far less inferences, theories, or systematic methods of discovery available, as a tool for steering one clear of unproductive paths, and towards more productive paths for improvement, than when making design changes in a metal stent.

It is recognized, therefore, that, whereas inferences previously accepted in the art for stent validation or feasibility when an isotropic and ductile metallic material was used, such inferences would be inappropriate for a polymeric stent. A change in a polymeric stent pattern may affect, not only the stiffness or lumen coverage of the stent in its deployed state, but also the propensity for fractures to develop when the stent is crimped or being deployed. This means that, in comparison to a metallic stent, there is generally no assumption that can be made as to whether a changed stent pattern may not produce an adverse outcome, or require a significant change in a processing step (e.g., tube forming, laser cutting, crimping, etc.). Simply put, the highly favorable, inherent properties of a metal (generally invariant stress/strain properties with respect to the rate of deformation or the direction of loading, and the material's ductile nature), which simplify the stent fabrication process, allow for inferences to be more easily drawn between a changed stent pattern and/or a processing step and the ability for the metallic stent to be reliably manufactured with the new pattern and without defects when implanted within a living being.

A change in the pattern of the struts and rings of a polymeric stent scaffolding that is plastically deformed, both when crimped to, and when later deployed by a balloon, unfortunately, is not as easy to predict as a metal stent. Indeed, it is recognized that unexpected problems may arise in polymer stent fabrication steps as a result of a changed pattern that would not have necessitated any changes if the pattern was instead formed from a metal tube. In contrast to changes in a metallic stent pattern, a change in polymer stent pattern may necessitate other modifications in fabrication steps or post-fabrication processing, such as crimping and sterilization.

A problem encountered with polymeric stents after they are crimped onto a balloon is the development of fractures and other defects that require the stent to be rejected and scrapped. Cracks and other defects can render the stent incapable of functioning properly when fully deployed by the balloon. Another problem is that deployment of polymeric stents from the crimped state to a deployed state in a patient can produce strain that adversely affects the ability of the stent to stay in the deployed state and remain at the implantation site, especially under cyclic loading conditions inherent in a patient's circulatory system. The strain induced during deployment can result in significant loss in radial strength.

In light of the foregoing, there is a need for a stent pattern and manufacturing method that reduces the cracks and other defects due to crimping and/or deployment. There is also a need for a stent pattern and manufacturing method that results in less strain when a stent is deployed for implantation.

SUMMARY OF THE INVENTION

Briefly and in general terms, the present invention is directed to an endoprosthesis and a method of making an endoprosthesis.

In aspects of the present invention, an endoprosthesis comprises a tubular network of struts cut from a radially expanded polymer tube. The tubular network comprises W-shaped closed cells, each W-shaped closed cell abutting six other W-shaped closed cells, ach W-shaped closed cell comprising ring struts, link struts, U-shaped hinge elements, and Y-shaped hinge elements. The ring struts form a plurality of ring structures, each ring structure connected to another one of the ring structures by at least one link strut. Each U-shaped hinge element connects exactly two ring struts to each other, the U-shaped hinge element being tangent to the two ring struts. Each Y-shaped hinge element connects a link strut to exactly two ring struts. Each ring structure has an overall curvilinear length from about 12 mm to about 15 mm.

In other aspect of the present invention, a method comprises cutting a radially expanded polymer tube to form a tubular network of struts. The tubular network comprises W-shaped closed cells. Each W-shaped closed cell abuts six other W-shaped closed cells. Each W-shaped closed cell comprises ring struts, link struts, U-shaped hinge elements, and Y-shaped hinge elements. The ring struts form a plurality of ring structures. Each ring structure is connected to another one of the ring structures by at least one link strut. Each U-shaped hinge element connects exactly two ring struts to each other, the U-shaped hinge element being tangent to the two ring struts. Each Y-shaped hinge element connects a link strut to exactly two ring struts. Each ring structure has an overall curvilinear length from about 12 mm to about 15 mm.

BRIEF DESCRIPTION OF THE DRAWINGS

FIG. 7 depicts a partial view of a ring from FIG. 4, showing the ring in a deformed configuration after being radially collapsed to a diameter less than the initial diameter.

FIG. 8 depicts a partial view of a ring from FIG. 4, showing the ring in another deformed configuration after manufacturing, the ring having been deployed at a diameter greater than the initial diameter.

DETAILED DESCRIPTION OF THE INVENTION

The various embodiments of the present invention relate to polymeric stents and methods of fabricating polymeric stents with favorable mechanical properties. The present invention can be applied to devices including, but is not limited to, self-expandable stents, balloon-expandable stents, stent-grafts, and grafts (e.g., aortic grafts).

Figure 1:
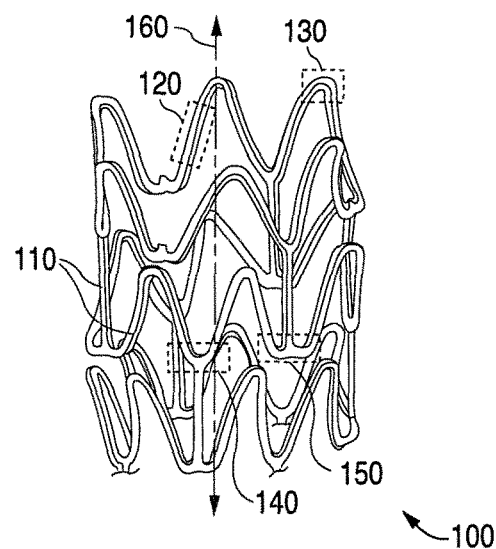
FIG. 1 depicts a stent.

FIG. 1 depicts a partial perspective view of an exemplary stent 100 that includes a pattern of a plurality of interconnecting structural elements or struts. Stent 100 has a cylindrical shape with an axis 160 and includes a pattern with a number of interconnecting structural elements or struts 110. Axis 160 extends through the center of the cylindrical shape. In general, a stent pattern is designed so that the stent can be radially compressed to allow for percutaneous delivery through an anatomical lumen, then deployed for implantation at the desired segment of the anatomical lumen. As used herein, deployment of the stent refers to radial expansion of the stent to implant the stent in the patient. The stresses involved during compression and deployment are generally distributed throughout various structural elements of the stent pattern.

The underlying structure or substrate of stent 100 is typically the primary source of the radial strength of the stent. The substrate can be completely or at least in part made from a biodegradable polymer or combination of biodegradable polymers, a biostable polymer or combination of biostable polymers, or a combination of biodegradable and biostable polymers. Additionally, a polymer-based coating applied over the substrate can include a biodegradable polymer or combination of biodegradable polymers, a biostable polymer or combination of biostable polymers, or a combination of biodegradable and biostable polymers.

Representative examples of polymers that may be used to fabricate or coat an implantable medical device of the present invention include, but are not limited to, poly(N-acetylglucosamine) (Chitin), Chitosan, poly(hydroxyvalerate), poly(lactide-co-glycolide), poly(hydroxybutyrate), poly(hydroxybutyrate-co-valerate), polyorthoester, polyanhydride, poly(glycolic acid), poly(glycolide), poly(L-lactic acid), poly(L-lactide), poly(D,L-lactic acid), poly(D,L-lactide), poly(caprolactone), poly(trimethylene carbonate), polyester amide, poly(glycolic acid-co-trimethylene carbonate), co-poly(ether-esters) (e.g. PEO/PLA), polyphosphazenes, biomolecules (such as fibrin, fibrinogen, cellulose, starch, collagen and hyaluronic acid), polyurethanes, silicones, polyesters, polyolefins, polyisobutylene and ethylene-alphaolefin copolymers, acrylic polymers and copolymers other than polyacrylates, vinyl halide polymers and copolymers (such as polyvinyl chloride), polyvinyl ethers (such as polyvinyl methyl ether), polyvinylidene halides (such as polyvinylidene chloride), polyacrylonitrile, polyvinyl ketones, polyvinyl aromatics (such as polystyrene), polyvinyl esters (such as polyvinyl acetate), acrylonitrile-styrene copolymers, ABS resins, polyamides (such as Nylon 66 and polycaprolactam), polycarbonates, polyoxymethylenes, polyimides, polyethers, polyurethanes, rayon, rayon-triacetate, cellulose, cellulose acetate, cellulose butyrate, cellulose acetate butyrate, cellophane, cellulose nitrate, cellulose propionate, cellulose ethers, and carboxymethyl cellulose. Another type of polymer based on poly(lactic acid)

that can be used includes graft copolymers, and block copolymers, such as AB block-copolymers ("diblock-copolymers") or ABA block-copolymers ("triblock-copolymers"), or mixtures thereof.

Additional representative examples of polymers that may be especially well suited for use in fabricating or coating an implantable medical device include ethylene vinyl alcohol copolymer (commonly known by the generic name EVOH or by the trade name EVAL), poly(butyl methacrylate), poly(vinylidene fluoride-co-hexafluororpropene) (e.g., SOLEF 21508, available from Solvay Solexis PVDF, Thorofare, N.J.), polyvinylidene fluoride (otherwise known as KYNAR, available from ATOFINA Chemicals, Philadelphia, Pa.), ethylene-vinyl acetate copolymers, and polyethylene glycol.

Stent 100 may be fabricated from a polymeric tube or a polymeric sheet that has been rolled and bonded to form a tube. A stent pattern may be formed on the polymeric tube or sheet by laser cutting away portions of the tube or sheet, leaving only struts and other members that function as scaffolding to support the walls of an anatomical lumen. Representative examples of lasers that may be used include, but are not limited to, excimer, carbon dioxide, and YAG. In other embodiments, chemical etching may be used to form a pattern on a tube.

The pattern of stent 100 in FIG. 1 allows for radial expansion and compression and longitudinal flexure. The pattern includes struts that are straight or relatively straight, an example being a portion 120. In addition, patterns may include bending elements 130, 140, and 150. Bending elements bend inward when a stent is crimped to allow radial compression of the stent in preparation for delivery through an anatomical lumen. Bending elements also bend outward when a stent is deployed to allow for radial expansion of the stent within the anatomical lumen. After deployment, stent 100 is subjected to static and cyclic compressive loads from the vessel walls. Thus, bending elements may deform during use.

As indicated above, a stent has certain mechanical requirements. A stent must have sufficient radial strength to withstand structural loads, namely radial compressive forces, imposed on the stent as it supports the walls of a vessel or other anatomical lumen. In addition, the stent must possess sufficient flexibility to allow for crimping, deployment, and cyclic loading. Also, a sufficiently low profile, that includes diameter and size of struts, is important. As the profile of a stent decreases, the easier is its delivery, and the smaller the disruption of blood flow.

Polymers tend to have a number of shortcomings for use as substrate materials for stents. Compared to metals, the strength to weight ratio of polymers is smaller than that of metals. A polymeric stent with inadequate radial strength can result in mechanical failure or recoil inward after implantation into a vessel. To compensate for the relatively low modulus of polymers as compared to metals, a polymeric stent requires significantly thicker struts than a metallic stent, which can result in an undesirably large profile.

Another shortcoming of polymers is that many polymers, such as biodegradable polymers, tend to be brittle under physiological conditions or conditions within a human body. Specifically, some biodegradable polymers that have a glass transition temperature, Tg, above human body temperature of about 37° C. exhibit a brittle fracture mechanism in which there is little or no plastic deformation prior to failure. As a result, a stent fabricated from such polymers can have insufficient toughness for the range of use of a stent. In particular, it is important for a stent to be resistant to fracture throughout the range of use of a stent, i.e., crimping, delivery, deployment, and during a desired treatment period.

A potential problem with polymeric stents is mechanical creep deformation. Creep refers to the gradual deformation of a structure subjected to an applied load. It is believed that the delayed response of polymer chains to stress causes creep by means of a phenomenon known as reptation. Reptation occurs when un-branched polymer chains slip past one another and away from the bulk entanglement in response to an applied load. This behavior in polymeric stents makes the response to stress less predictable than in metallic stents. Creep can cause a deployed stent to retract or recoil radially inward, reducing the effectiveness of a stent in maintaining desired vascular patency.

To address these and other problems, the mechanical properties of a polymer can be modified through various processing techniques, such as, by applying stress to a polymer. The application of stress can induce molecular orientation along the direction of stress which can modify mechanical properties along the direction of applied stress. For example, strength and modulus are some of the important properties that depend upon orientation of polymer chains in a polymer. Molecular orientation refers to the relative orientation of polymer chains along a longitudinal or covalent axis of the polymer chains.

A polymer may be completely amorphous, partially crystalline, or almost completely crystalline. A partially crystalline polymer includes crystalline regions separated by amorphous regions. The crystalline regions do not necessarily have the same or similar orientation of polymer chains. However, a high degree of orientation of crystallites may be induced by applying stress to a semi-crystalline polymer. The stress may also induce orientation in the amorphous regions. An oriented amorphous region also tends to have high strength and high modulus along an axis of alignment of polymer chains. Additionally, for some polymers under some conditions, induced alignment in an amorphous polymer may be accompanied by crystallization of the amorphous polymer into an ordered structure. This is known as stress induced crystallization.

As indicated above, due to the magnitude and directions of stresses imposed on a stent during use, it is important for the mechanical stability of the stent to have suitable mechanical properties, such as strength and modulus, in the axial and circumferential directions. Therefore, it can be advantageous to modify the mechanical properties of a polymeric tube or sheet substrate, to be used in the fabrication of a stent pattern, by induced orientation from applied stress in the axial direction, circumferential direction, or both. Since highly oriented regions in polymers tend to be associated with higher strength and modulus, it may be desirable to incorporate processes that induce alignment of polymer chains along one or more preferred axes or directions into fabrication of stents.

The degree of radial expansion, and thus induced circumferential orientation and radial strength, of a tube can be quantified by a radial expansion ratio:

$$RE = (\text{Inside Diameter of Expanded Tube, ID}_E) / (\text{Original Inside Diameter of Tube, ID}_O)$$

The RE ratio can also be expressed as a percent expansion:

$$\% RE = (RE - 1) \times 100\%$$

In some embodiments, a stent substrate in the form of a polymeric tube may be deformed by blow molding. In blow molding, the tube can be radially deformed or expanded by increasing a pressure in the tube by conveying a fluid into the tube. The fluid may be a gas, such as air, nitrogen, oxygen, or argon. The polymer tube may be deformed or extended axially by applying a tensile force by a tension source at one end while holding the other end stationary. Alternatively, a tensile force may be applied at both ends of the tube. The tube may be axially extended before, during, and/or after radial expansion.

In some embodiments, blow molding may include first positioning a tube in a tubular mold. The mold may act to control the degree of radial deformation of the tube by limiting the deformation of the outside diameter or surface of the tube to the inside diameter of the mold. The inside diameter of the mold may correspond to a diameter less than or equal to a desired diameter of the polymer tube. Alternatively, the fluid temperature and pressure may be used to control the degree of radial deformation by limiting deformation of the inside diameter of the tube as an alternative to or in combination with using the mold. The temperature of the tube can be heated to temperatures above the Tg of the polymer during deformation to facilitate deformation. The polymer tube may also be heated prior to, during, and subsequent to the deformation.

Properties of a polymer such as fracture toughness are affected by the overall degree of crystallinity and the number and size of crystal domains in a semi-crystalline polymer. It has been observed that fracture toughness is increased by having a large number of small crystal domains in a polymer surrounded by an amorphous domain. Such a crystal structure can also reduce or prevent creep.

Figure 2:
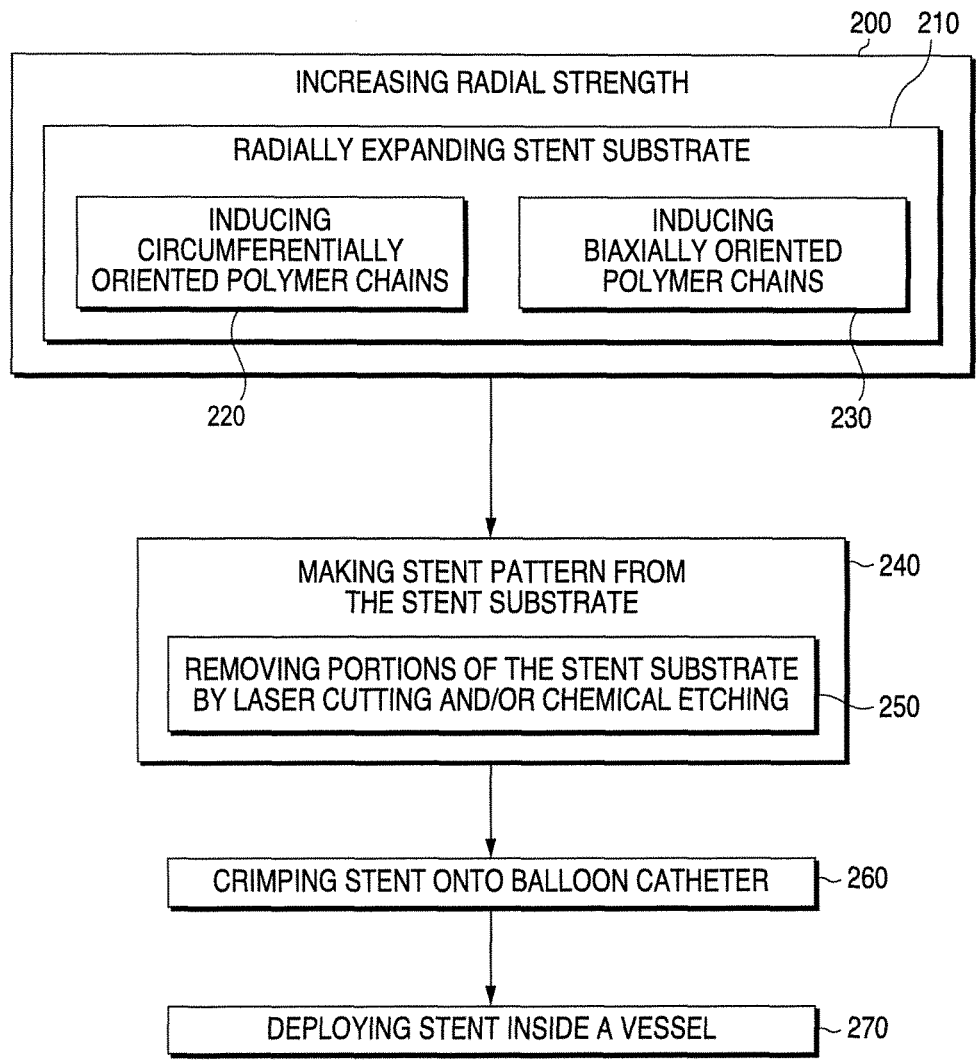
FIG. 2 depicts a process flow diagram in accordance with an embodiment of the present invention.

FIG. 2 shows a method of manufacturing stents in accordance with an embodiment of the present invention. The method comprises increasing 200 the radial strength of the stent substrate in order to eliminate or reduce inward recoil of a stent manufactured from the substrate. The stent substrate can be a polymeric tube or sheet. Increasing 200 the radial strength may include radially expanding 210 the stent substrate. Radial expansion 210 may induce 220 polymer chains in individual stent struts later formed from the substrate to have a preferential orientation in a circumferential direction as compared to an axial direction. The axial direction or orientation corresponds to the overall lengthwise direction of the stent as represented by axis 160 in FIG. 1 and line A-A in FIGS. 3 and 4. The circumferential direction or orientation corresponds to the direction along the circumference of the stent substrate as represented by line B-B in FIGS. 3 and 4 and circle 728 in FIG. 5.

Radial expansion 210 may be achieved by blow molding a stent substrate that is in the form of a polymer tube. Prior to radial expansion 210, the tube has an original inner diameter of $ID_O$. After radial expansion 210, the expanded tube has an inner diameter of $ID_E$. In some embodiments, radial expansion 210 is performed so that the percent radial expansion % RE (equal to $(ID_E/ID_O-1) \times 100\%$) is between about 300% and 400%, which corresponds to $ID_E$ between about four times $ID_O$ and about five times $ID_O$. In other embodiments, % RE is between about 400% and 500%, which corresponds to $ID_E$ between about five times $ID_O$ and about six times $ID_O$. In yet other embodiments, radial expansion 210 is performed until % RE is about 500%, or greater, which corresponds to $ID_E$ that about six times $ID_O$, or greater.

Polymer chains in a stent substrate may initially have a preferential orientation in the axial direction as a result of extrusion, injection molding, tensile loading, machining, or other process used to form the stent substrate. In some embodiments, radial expansion 210 of a stent substrate having polymer chains with an initial axial orientation will reorient or induce 220 the polymer chains to have a circumferential orientation. In other embodiments, radial expansion 210 of a stent substrate having polymers with an initial axial orientation may induce 230 polymer molecule chains to have a biaxial orientation. In a biaxial orientation, the polymer chains are oriented in a direction that is neither preferentially circumferential nor preferentially axial. In this way, the polymer chains can be oriented in a direction substantially parallel to the lengthwise axis of individual stent struts so as to increase the overall radial strength of the stent.

The words "substantially" or "substantial" as used herein to modify a condition means that the condition is present in absolute or perfect form, as well as in a form that is not necessarily absolute or perfect but would be considered close enough to those of ordinary skill in the art to warrant designating the condition as still being present. For example, "substantially parallel" encompasses perfectly parallel as well as not perfectly parallel but parallel enough to those of ordinary skill in the art to warrant designating the parallel condition as being present.

Figure 3:
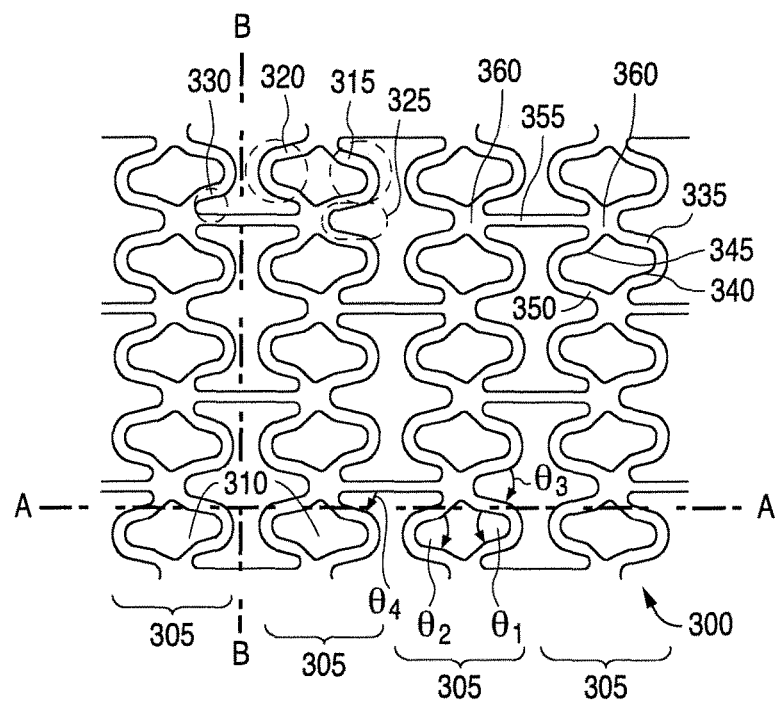
FIG. 3 depicts a stent pattern viewed in a flat or planar state.
Figure 4:
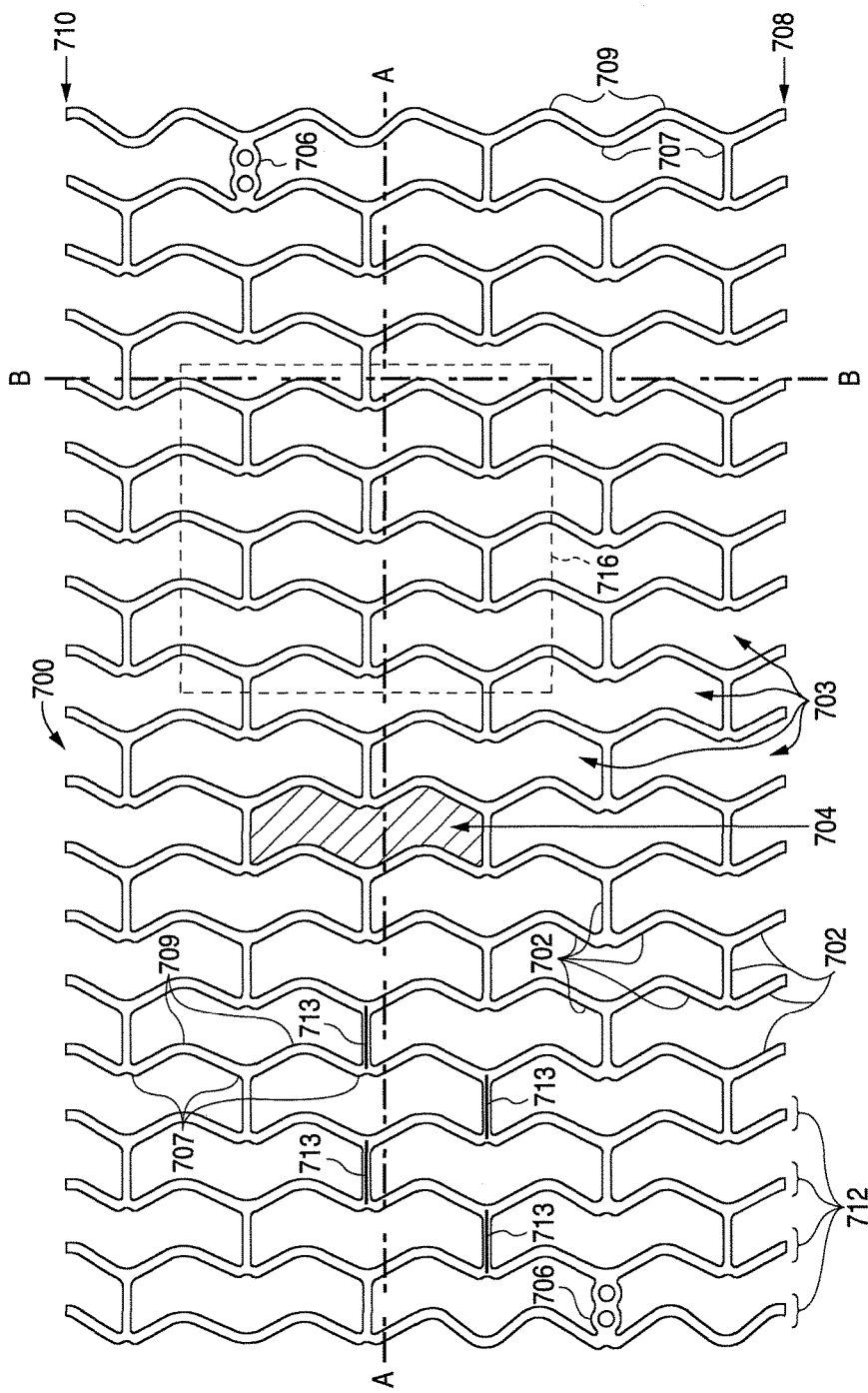
FIG. 4 depicts another stent pattern viewed in a flat or planar state.

The method also includes making 240 a stent pattern from the substrate after inducing polymer chains to have a particular preferential orientation. Making 240 the stent pattern may include removing 250 portions of the substrate by laser cutting and/or chemical etching, leaving only stent struts, bending elements, and other necessary structures. The desired strength, toughness, and/or flexibility of individual structural elements in the stent pattern can achieved by forming such elements substantially parallel with the orientation of the polymer molecule chains. The stent pattern can be as shown in FIGS. 3 and 4 or variations of FIGS. 3 and 4.

Optionally, after making 240 the stent pattern, the stent may be crimped 260 onto a balloon catheter or other stent delivery device. Prior to or during crimping 260, the stent may be heated to a crimping temperature Tc. In some embodiments, Tc is greater than ambient room temperature Ta to minimize or prevent outward recoil of the stent to a larger diameter after crimping. Outward recoil undesirably increases the delivery profile of the stent and may cause the stent to prematurely detach from the catheter during delivery to a target treatment site within a vessel. Also, Tc is preferably below Tg to reduce or eliminate stress relaxation during crimping. Stress relaxation during or after crimping leads to a greater probability of cracking during subsequent deployment of the stent. To reduce or prevent such cracking, the difference between Tc and Tg can be maximized by increasing Tg through stress induced crystallization.

After manufacturing, the stent can be deployed 270 inside a blood vessel from a crimped diameter to a deployed outer diameter $OD_D$. In some embodiments, $OD_D$ is greater than $OD_E$, the outer diameter as a result of radial expansion of the stent substrate. Preferably, $OD_D$ is selected so that no cracks are formed in the stent during deployment. In some embodiments, $OD_D$ is 3.5 mm (0.1378 in). In other embodiments, $OD_D$ is 4.0 mm (0.1575 in).

If the stent was crimped 260 onto a balloon catheter, the deployment 270 of the stent can include inflating the balloon catheter to urge the stent to move from its crimped configuration to an expanded, deployed configuration. In other embodiments, the stent may be self-expanding and deployment 270 of the stent can include removing a sheath or other constraining device from around the stent to allow the stent to self-expand.

It will be appreciated that the method of FIG. 2 is applicable to many types of bodily lumens or organs. Examples of such organs include, but are not limited to, vascular organs such as, for example, coronary arteries or hepatic veins; renal organs such as, for example, urethras and ureters; biliary organs such as, for example, biliary ducts; pulmonary organs such as, for example, tracheas, bronchi and bronchioles; and gastrointestinal organs such as, for example, esophagi and colons.

FIG. 3 depicts an exemplary stent pattern 300 cut from a polymeric substrate. Stent pattern 300 is shown in a flattened condition so that the pattern can be clearly viewed. When the stent pattern 300 is in a cylindrical form, it forms a radially expandable stent. Stent pattern 300 includes a plurality of cylindrical rings 305 with each ring including a plurality of diamond shaped cells 310. Embodiments of stent pattern 300 may have any number of rings 305 depending on a desired length of a stent. For reference, line A-A extends in an longitudinal or axial direction, which is the same direction of axis 160 in FIG. 1. Diamond shaped cells 310 include bending elements 315 and 320. Stent pattern 300 can also includes bending elements 325 and 330. The angles of bending elements 315, 320, 325, and 330 correspond to angles $\theta_1$, $\theta_2$, $\theta_3$, and $\theta_4$. Angles $\theta_1$, $\theta_2$, $\theta_3$, and $\theta_4$ are equivalent to or about 42, 42, 41, and 21 degrees, respectively. In other embodiments, angles $\theta_1$, $\theta_2$, $\theta_3$ are about 24 degrees to about 29 degrees, and angle $\theta_4$ is about 12 degrees to about 15 degrees. Diamond shaped cells 310 are made up of bar arms 335 and 340 that form bending element 315 and bar arms 345 and 350 that form bending element 320.

When stent 300 is crimped, bending elements 315, 320, 325, and 330 flex inward and angles $\theta_1$, $\theta_2$, $\theta_3$, and $\theta_4$ decrease, allowing the stent to be radially compressed. With respect to bending elements 315, 320, and 325, struts on either side of the bending elements bend toward each other. However, in bending element 330, the strut of the diamond-shaped element tends to bend toward a linking arm 355, which tends to remain relatively parallel to the longitudinal axis during crimping.

Pattern 300 includes linking arms 355 that connect adjacent cylindrical rings. Linking arms 355 are parallel to line A-A and connect adjacent rings between intersection 360 of circumferentially adjacent diamond-shaped elements 310 of one ring and intersection 360 of circumferentially adjacent diamond shaped elements 310 of an adjacent ring. As shown, linking elements connect every other intersection along the circumference.

The curved portions of bending elements experience substantial stress and strain when a stent is crimped and deployed. Therefore high strength and toughness are very important in these regions. Ideally, the most effective polymer chain orientation to improve fracture toughness is along the length of the axis of the strut. Radial expansion imparts orientation and fracture toughness along the circumferential direction, as shown by line B-B.

FIG. 4 shows another stent pattern 700 in accordance with an embodiment of the present invention. The stent pattern 700 includes various struts 702 oriented in different directions and gaps 703 between the struts. Each gap 703 and the struts 702 immediately surrounding the gap 703 defines a closed cell 704. At the proximal and distal ends of the stent, a strut 706 includes depressions, blind holes, or through holes adapted to hold a radiopaque marker that allows the position of the stent inside of a patient to be determined.

One of the cells 704 is shown with cross-hatch lines to illustrate the shape and size of the cells. In the illustrated embodiment, all the cells 704 have the same size and shape. In other embodiments, the cells 704 may vary in shape and size.

The stent pattern 700 is shown in a planar or flattened view for ease of illustration and clarity, although the stent pattern 700 on a stent actually extends around the stent so that line A-A is substantially parallel to the central axis of the stent. The pattern 700 is illustrated with a bottom edge 708 and a top edge 710. On a stent, the bottom edge 708 meets the top edge 710 so that line B-B forms a circle around the stent. In this way, the stent pattern 700 forms sinusoidal hoops or rings 712 that include a group of struts arranged circumferentially. The rings 712 include a series of crests 707 and troughs 709 that alternate with each other. The sinusoidal variation of the rings 712 occurs primarily in the axial direction, not in the radial direction. That is, all points on the outer surface of each ring 712 are at substantially the same radial distance away from the central axis of the stent.

Still referring to FIG. 4, the rings 712 are connected to each other by another group of struts that have individual lengthwise axes 713 substantially parallel to line A-A. The rings 712 are capable of being collapsed to a smaller diameter during crimping and expanded to their original diameter or to a larger diameter during deployment in a vessel.

In other embodiments, the stent may have a different number of rings 712 and cells 704 than what is shown in FIG. 4. The number of rings 712 and cells 704 may vary depending on the desired axial length and deployed diameter of the stent. For example, a diseased segment of a vessel may be relatively small so a stent having a fewer number of rings can be used to treat the diseased segment.

Figure 5:
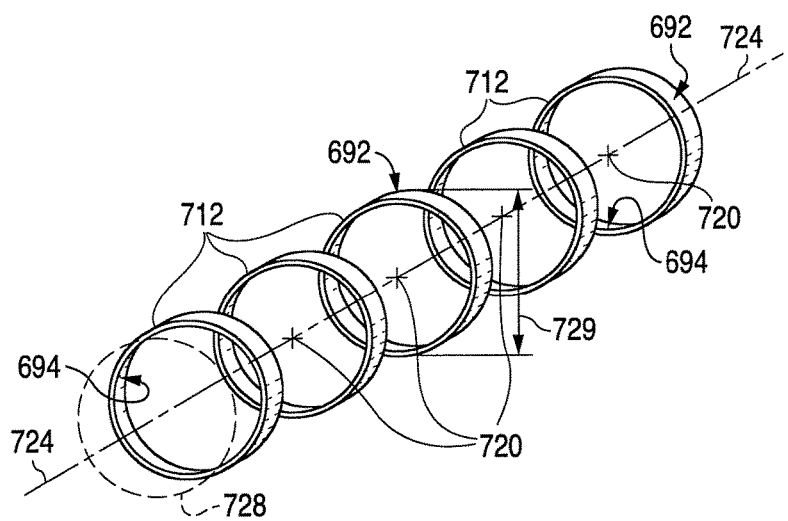
FIG. 5 depicts a simplified view of the stent pattern of FIG. 4 in a cylindrical state.
Figure 6:
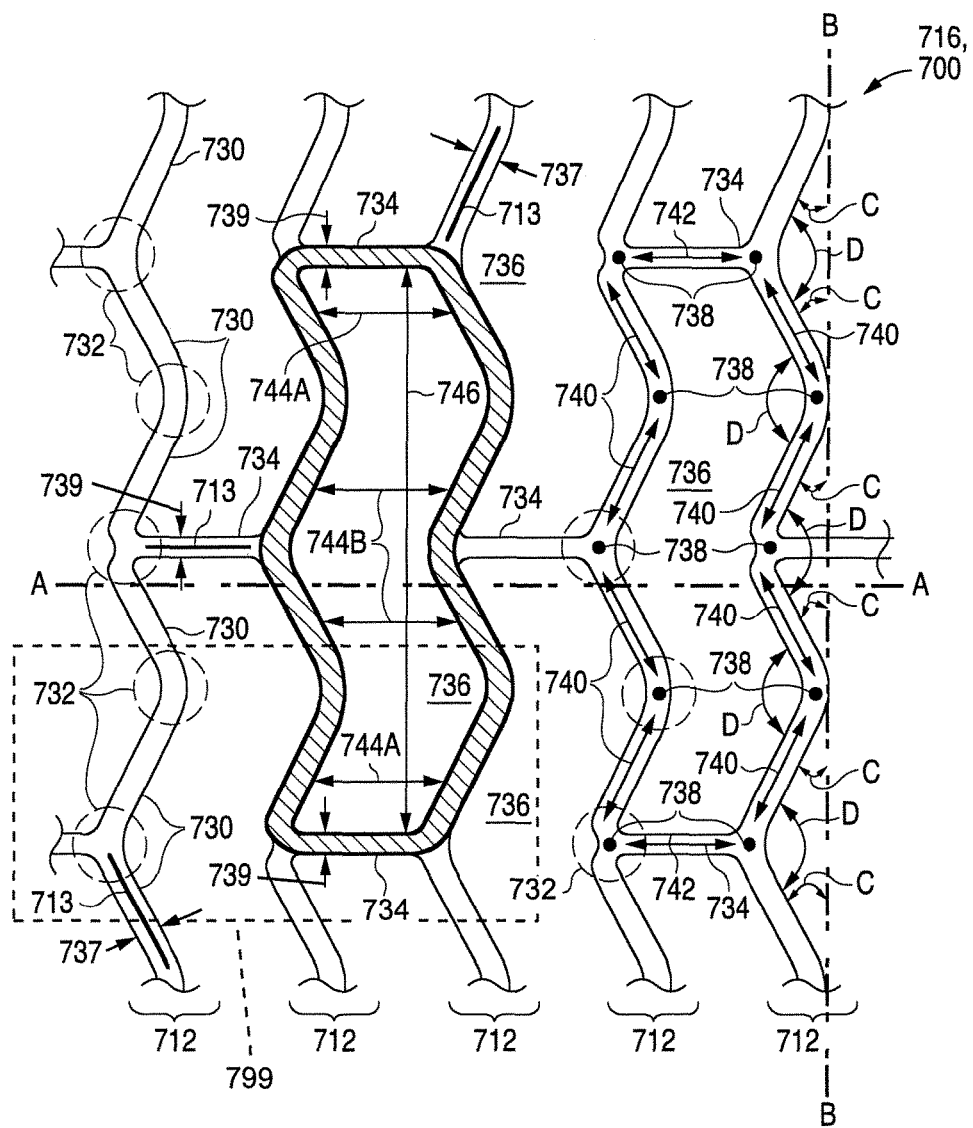
FIG. 6 depicts a detailed view of a portion of the stent pattern of FIG. 4, showing rings in a non-deformed configuration, the rings having an initial diameter.

FIG. 5 shows a simplified diagram of the stent pattern 700 in the form of a cylindrical tube. The sinusoidal variation of the rings 712 and the struts linking the rings to each other are omitted for clarity. The rings 712 have center points 720. At least two of the center points 720 define the central axis 724 of the stent. The central axis 724 and line A-A in FIGS. 4 and 6 are substantially parallel to each other. The rings have an abluminal surface 692 and a luminal surface 694. The abluminal surface 692 faces outward and normally contacts the wall of the anatomical lumen in which the stent is deployed. The luminal surface 694 faces inward toward the center of the lumen when deployed.

FIG. 6 shows a detailed view of a portion 716 of the stent pattern 700 of FIG. 4. The rings 712 include linear ring struts 730 and curved hinge elements 732. The ring struts 730 are connected to each other by the hinge elements 732. In some embodiments, the ring struts and hinge elements are formed from a polymeric substrate that was radially expanded in the circumferential direction represented by a dotted circle 728 in FIG. 5 and line B-B in FIGS. 4 and 6.

Radial expansion of the substrate used to form the stent pattern 700 is preferably between about 300% and about 700%, which corresponds to $ID_E$ that is between about four to about eight times $ID_O$. In some embodiments, radial expansion is between about 400% and about 600%, which corresponds to $ID_E$ that is between about five to about seven times $ID_O$. In other embodiments, radial expansion is at or about 500%, which corresponds to $ID_E$ that is at or about six times $ID_O$.

The hinge elements 732 are adapted to flex, which allows the rings 712 to move from a non-deformed configuration to a deformed configuration. As used herein, "non-deformed configuration" refers to the state of the rings prior to being crimped to a smaller diameter for delivery through an anatomical lumen. For example, in embodiments in which a stent is formed by laser cutting a radially expanded polymer tube, the non-deformed configuration is the state of the rings after radial expansion of the polymer tube and laser cutting of the polymer tube to form the rings. As used herein, "deformed configuration" refers to the state of the rings upon some type of deformation, such as crimping or deployment.

FIGS. 3-6 show the rings 712 in the non-deformed configuration. Referring to FIG. 5, the rings 712 have an initial outer diameter 729 when in the non-deformed configuration. In some embodiments, the initial outer diameter 729 of the rings 712 is substantially equivalent to $OD_E$, the outer diameter of the stent substrate after the stent substrate is radially expanded (outer diameter of expanded tube).

Referring again to FIG. 6, line B-B lies on a reference plane perpendicular to the central axis 724 (FIG. 5). When the rings 712 are in the non-deformed configuration, as shown in FIG. 6, each ring strut 730 is oriented at a non-zero angle C relative to the reference plane. The non-zero angle C is less than 40 degrees in the illustrated embodiment. Preferably, the non-zero angle C is less than 35 degrees, and more narrowly the angle C is between about 25 degrees and about 28 degrees. In other embodiments, the angle C can have other values.

Also, the ring struts 730 are oriented at an interior angle D relative to each other. The interior angle D is greater than 100 degrees in the illustrated embodiment. Preferably, the interior angle D is greater than 110 degrees, and more narrowly, the angle D is between about 124 degrees and about 130 degrees. In other embodiments, the interior angle D can have other values.

Referring once again to FIG. 6, the stent also includes link struts 734 connecting the rings 712 together. The link struts 734 are oriented substantially parallel to line A-A and the central axis 724 (FIG. 5). The ring struts 730, hinge elements 732, and link struts 734 define a plurality of W-shaped closed cells 736. The boundary or perimeter of one W-shaped cell 736 is darkened in FIG. 6 for clarity. The W-shapes appear rotated 90 degrees counterclockwise. Each of the W-shaped cells 736 is immediately surrounded by six other W-shaped cells 736, meaning that the perimeter of each W-shaped cell 736 merges with a portion of the perimeter of six other W-shaped cells 736. Stated another way, each W-shaped cell 736 abuts or touches six other W-shaped cells 736.

The perimeter of each W-shaped cell 736 includes eight of the ring struts 730, two of the link struts 734, and ten of the hinge elements 732. Four of the eight ring struts form a proximal side of the cell perimeter and the other four ring struts form a distal side of the cell perimeter. The opposing ring struts on the proximal and distal sides are substantially parallel to each other.

Figure 10:
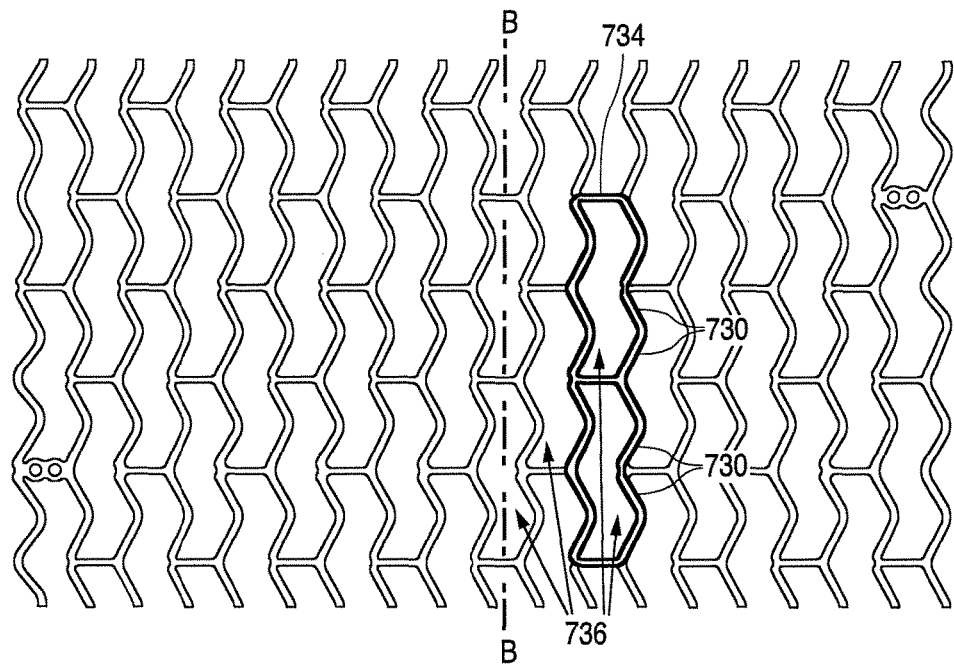
FIG. 10 depicts a stent pattern viewed in a flat or planar state, the stent pattern having W-shaped cells having varying sizes in the circumferential direction.

Within each of the hinge elements 732 there is an intersection point 738 toward which the ring struts 730 and link struts 734 converge. There is an intersection point 738 adjacent each end of the ring struts 730 and link struts 734. Distances 740 between the intersection points adjacent the ends of rings struts 730 are substantially the same for each ring strut 730. In other embodiments, such as shown in FIG. 10, some of the ring struts 730 may be longer than other ring struts 730 so that distances 740 may vary. For example, distances 740 may vary to allow for a variation in mechanical characteristics at different portions of the stent.

Figure 11:
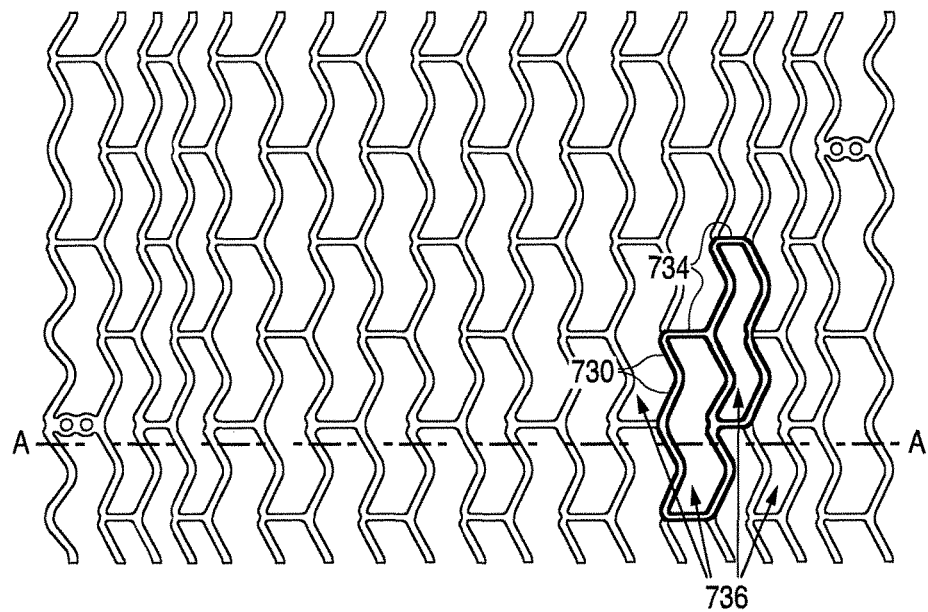
FIG. 11 depicts a stent pattern viewed in a flat or planar state, the stent pattern having W-shaped cells having varying sizes in the axial direction.

Referring again to FIG. 6, distances 742 between the intersection points adjacent the ends of horizontal link struts 734 are substantially the same for each link strut 734. In other embodiments, such as shown in FIG. 11, some of the link struts 734 may be longer than other link struts 734 so that distances 742 may vary to allow for a variation in mechanical characteristics at different portions of the stent.

Also, distances 740 are substantially the same as distances 742. In other embodiments, distances 740 and 742 are different from each other to allow for a variation in mechanical characteristics at different portions of the stent.

The ring struts 730 have widths 737 that are uniform along the individual lengthwise axis 713 of the ring strut. The link struts 734 have widths 739 that are also uniform along the individual lengthwise axis 713 of the link strut.

As shown in FIG. 6, the interior space of each W-shaped cell 736 has an axial dimension 744 parallel to line A-A and a circumferential dimension 746 parallel to line B-B. The axial dimension 744 is substantially constant with respect to circumferential position. That is, axial dimensions 744A adjacent the top and bottom ends of the cells 736 are substantially the same as axial dimensions 744B further away from the ends. The constant axial dimension 744 provides an improved strut distribution compared to the stent pattern of FIG. 3.

In the illustrated embodiment of FIG. 6, axial and circumferential dimensions 744 and 746 are the same among the W-shaped cells 736. In other embodiments, the axial dimension 744 and/or circumferential dimension 746 may differ among cells 736 to allow for a variation in mechanical characteristics at different portions of the stent.

FIGS. 7 and 8 show a portion of one ring 712 in two different deformed configurations. In FIG. 7, the ring 712 has been radially compressed to a diameter less than its initial outer diameter 729 (FIG. 5), such as when the stent is crimped onto a catheter. During such compression, the ring struts 730 pivot about the hinge elements 732 so that the ring struts 730 fold toward each other and become oriented at an angle E relative to the reference plane represented by line B-B. Angle E is greater than corresponding angle C in FIG. 6 which shows rings 712 in the non-deformed configuration. Also, the ring struts 730 are oriented at an interior angle F relative to each other. Angle F is less than corresponding angle D in FIG. 6.

In FIG. 8, the ring 712 has been radially expanded, after manufacturing, to a deployed configuration. Radial expansion of the rings 712 is not to be confused with radial expansion of the stent substrate during manufacturing. When the ring 712 is radially expanded, ring struts 730 pivot about the hinge elements 732 and the ring struts 730 become oriented at an angle G relative to the reference plane represented by line B-B. When the ring 712 is expanded to a diameter greater than its non-deformed initial diameter 729 (FIG. 5), angle G is less than corresponding angle C in FIG. 6. Also, the ring struts 730 are oriented at an interior angle H relative to each other. Angle H is greater than corresponding angle D in FIG. 6.

Figure 9:
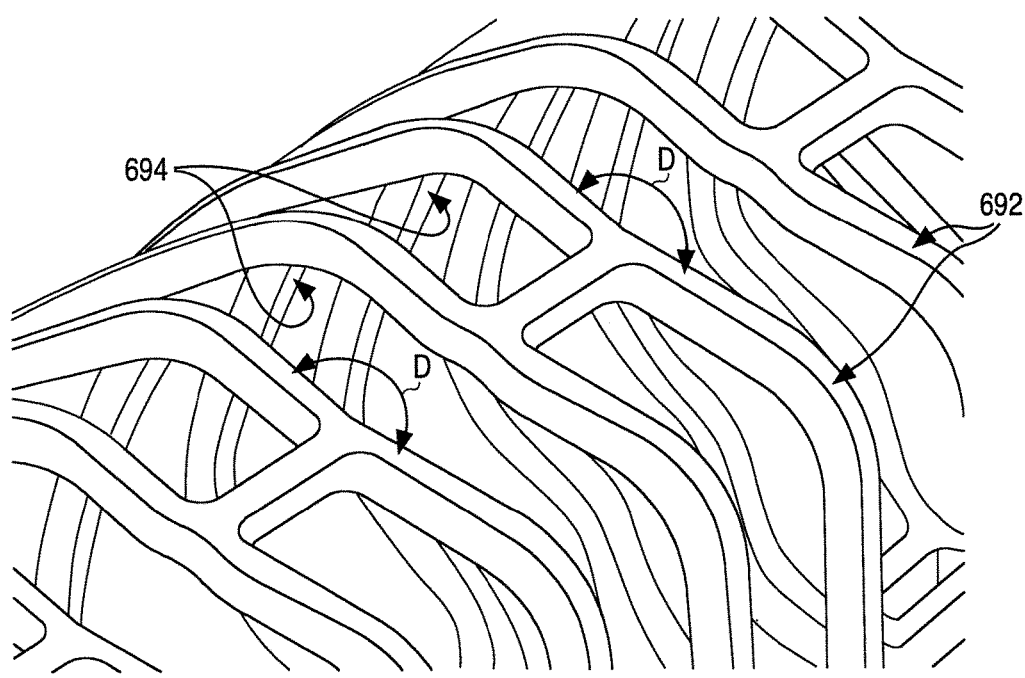
FIG. 9 depicts a perspective view of a stent having the stent pattern of FIG. 4.

A test was performed to study long term lumen patency using different stent patterns formed from polymer tube substrates that were radially expanded during manufacturing. Case 1 corresponds to a stent having the stent pattern of FIG. 2 cut from a polymer tube substrate that was previously radially expanded 300% to a diameter of 2.13 mm (0.084 inches). Case 2 corresponds to a stent having the stent pattern of FIGS. 4 and 6 cut from a polymer tube substrate that was previously radially expanded 500% to a diameter of 3.48 mm (0.137 inches). In both cases, the polymer tube was an extruded tube of poly(L-lactide), a bioabsorable polymer. FIG. 9 is a perspective view of a portion of the stent of Case 2.

In Case 1, ring struts 335, 340, 345, and 350, when in the non-deformed configuration, were at about 75 degrees to about 78 degrees relative to the circumferential direction, that is the direction of radial expansion. Also, ring struts 335 and 345 were oriented relative to ring struts 340 and 350 at interior angles ($\theta_1$ and $\theta_3$ in FIG. 3) of about 24 degrees to about 29 degrees.

In Case 2, ring struts 730, when in the non-deformed configuration, were at 25 degrees to 28 degrees from the circumferential direction. Also, ring struts 730 were oriented relative to each other at an interior angle (angle D in FIG. 6) of about 124 degrees to about 130 degrees.

Compared to Case 1, Case 2 exhibited less inward recoil (decrease in diameter) after deployment, resulting in larger lumens and better stent apposition or contact with surrounding tissue. The results of the test indicate that 500% radial expansion combined with struts arranged in the pattern of FIGS. 4 and 6 (Case 2) provided greater radial strength than 300% radial expansion combined with struts arranged in the pattern of FIG. 3 (Case 1). The results were unexpected in that excessive radial expansion of the substrate is known to cause an increase in strut fractures during crimping or upon deployment, and that excessively large interior angles are known to prevent stents from crimping easily and in a controlled manner.

It is believed that the polymer chains in Case 1 do not readily line up with the rings as compared to Case 2, leading to a stent that is less resistant to mechanical creep deformation as compared to Case 2. With 500% radial expansion in Case 2, the polymer chains are substantially circumferentially oriented. The interior angles between stent struts in Case 2 allow the stent struts to line up well with the circumferentially oriented polymer chains. It is also believed that smaller interior angles than those in Case 2 would increase the likelihood of fractures since expansion loads would be applied against the "grain" of the substrate, that is, against the circumferential orientation of the polymer chains.

In other tests, stents were made from tubes of poly(L-lactide) substrate that were radially expanded to different levels, namely 400%, 500%, 600%, and 700%. The stents were crimped at different crimping temperatures, deployed, then inspected for fractures. At a crimping temperature of about 50° C., the group of stents made from 500% radially expanded tubes had the lowest average number of fractures. At crimping temperatures of about 30° C., 50° C., and 60° C., the group of stents made from 700% radially expanded tubes had the highest average number of fractures.

Non-Polymeric Materials

It will be appreciated that the above disclosed stent patterns may be applied to non-polymer stent substrates as well. A non-polymer substrate of a stent may be made of a metallic material or an alloy such as, but not limited to, cobalt chromium alloy (ELGILOY), stainless steel (316L), high nitrogen stainless steel, e.g., BIODUR 108, cobalt chrome alloy L-605, "MP35N," "MP20N," ELASTINITE (Nitinol), tantalum, nickel-titanium alloy, platinum-iridium alloy, gold, magnesium, or combinations thereof "MP35N" and "MP20N" are trade names for alloys of cobalt, nickel, chromium and molybdenum available from Standard Press Steel Co., Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum.

Hinge Element Details

Figure 12:
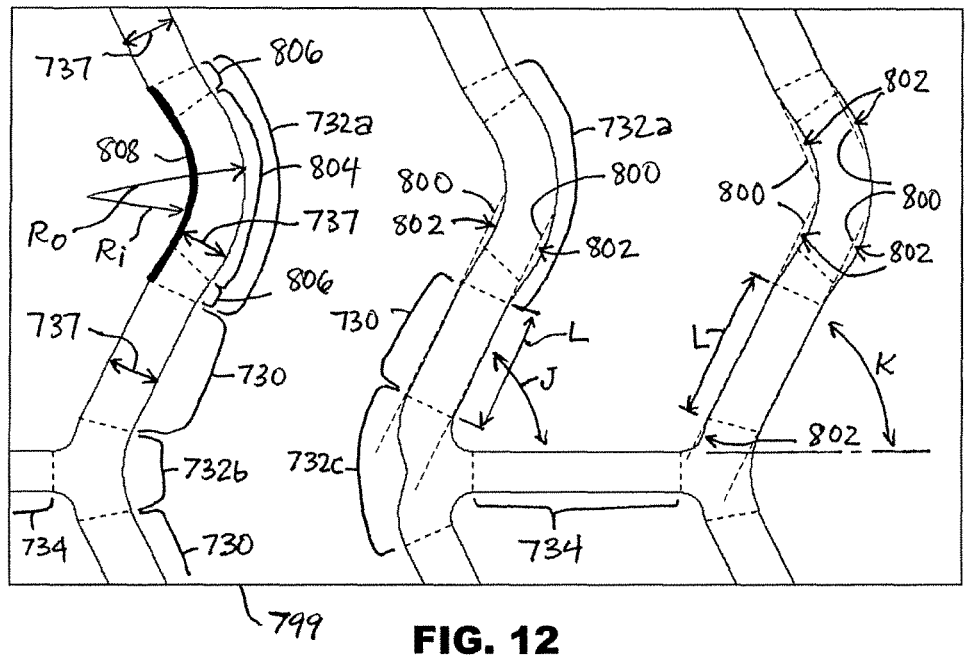
FIG. 12 depicts a detailed view of a portion of the stent pattern of FIG. 6, showing U-shaped hinge elements that are non-tangent to linear ring struts.

FIG. 12 shows a detailed view of linear ring struts 730, hinge elements 732, and linear link struts 734 of the pattern shown in FIGS. 4 and 6. FIG. 12 corresponds to the boxed area 799 in FIG. 6, and FIG. 6 corresponds to the boxed area 716 in FIG. 4. In FIG. 12, every hinge element 732 is directly connected to exactly two linear ring struts 730. There are two types of hinge elements 732: U-shaped hinge elements 732a, and Y-shaped hinge elements 732b, 732c. A hinge element is U-shaped when it has exactly two ends and is Y-shaped when it has exactly three ends. The U-shaped hinge elements 732a connect two linear ring struts 730 together, exclusively. The Y-shaped hinge elements 732b, 732c connect two linear ring struts 730 and a linear link strut 734 together, exclusively. There is a Y-shaped hinge element at each end of every linear link strut 734.

The U-shaped hinge elements 732a are not tangent to the linear ring struts 730. The non-tangent relationship can be seen from reference lines 800 (illustrated as broken lines) which coincide with and extend out from the straight edges of linear ring struts 730. The edges of the struts are illustrated as solid lines. The U-shaped hinge elements 732a bow out from the linear ring struts 730 in such a way that there are clearly noticeable interior spaces 802 between the reference lines 800 and the edges of the U-shaped hinge elements 732a which cross over the reference lines 800.

Still referring to FIG. 12, each U-shaped hinge element 732a includes a middle segment 804 and two end segments 806. Broken lines are illustrated to show boundaries between the middle and end segments. Each middle segment 804 has edges that are curved continuously throughout. The end segments 806 have edges that are straight throughout. The end segments 806 provide a geometric transition from the linear ring struts 730 to the middle segment 804 of the U-shaped hinge element 732a.

Due to its non-tangency, the U-shaped hinge elements 732a have more material than would otherwise be possible for a given bend radius. Stated differently, a non-tangent U-shaped hinge element 732a of a given bend radius, as shown in FIG. 12, has more material than a similarly located tangent U-shaped hinge element of the same bend radius. A way to measure the amount of material is to measure the length of the inside curve 808 of the U-shaped hinge elements 732a. The inside curve of one U-shaped hinge element 732a is illustrated as a thick line to distinguish it from other features of the stent pattern.

This additional material can help reduce cracks at the hinge elements when a stent is expanded from a crimped state to a fully deployed state, especially when the stent at a fully deployed state (e.g., block 270 in FIG. 2) is greater in diameter than the stent prior to crimping (e.g., block 250 in FIG. 2). As previously mentioned, a stent can be formed by radially expanding a stock tube to make a precursor tube having a selected outer diameter $OD_E$, then a stent pattern is cut onto the precursor tube (e.g., block 250 in FIG. 2), followed by crimping to a smaller diameter and subsequent radial expansion to a deployed diameter $OD_D$ (e.g., block 270 in FIG. 2). For various reasons, it may be desirable to over-expand the stent so that $OD_D$ is greater than $OD_E$, such to address a problem with post-deployment recoil of the sent. The additional material provided by the non-tangent hinge elements 732a allows the stent to expand to $OD_D$ greater than $OD_E$ with a lower incidence of cracks. Also, stresses in the non-tangent hinge elements 732a during stent deployment are distributed over a greater amount of material, which may also reduce the incidence of cracks.

Referring to FIG. 12, the linear link struts 730 have overall lengths L, which can be measured as the length of one of the straight edges of the strut. Also, the linear ring struts 730 are oriented relative to the linear link struts 734 at the same angles. Each linear link strut 734 is connected to a first ring strut 730 and a second ring strut 730. The first and second ring struts are connected to opposite ends of the linear link strut. The first ring strut is oriented at an angle J relative to the link strut. The second ring strut is oriented at an angle K relative to the link strut. Angles J and K are substantially the same. Also, the linear ring struts 730 and the U-shaped hinge elements 732a have a width 737 that is substantially uniform throughout the linear ring struts and U-shaped hinge elements. The width is generally axial (as opposed to radial) in direction and is measured normal or perpendicular to an edge of the hinge element or ring strut.

Figure 13:
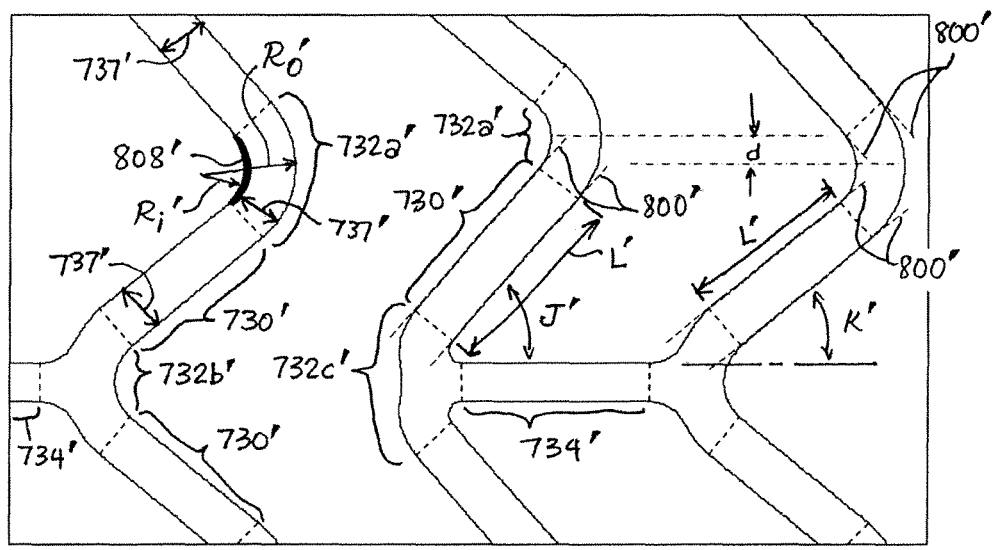
FIG. 13 depicts a detailed view of a portion of a stent pattern, showing U-shaped hinge elements that are tangent to linear ring struts.

FIG. 13 shows another embodiment of a stent pattern having repeating W-shaped closed cells similar to FIGS. 4 and 6 in that the cells are arranged in an offset brick pattern. There are linear ring struts 730', hinge elements 732', and linear link struts 734'. There are U-shaped hinge elements 732a' located circumferentially between the linear link struts 734', and Y-shaped hinge elements 732b', 732c' located at the ends of the linear link struts 734'. Broken lines are illustrated to show boundaries of the hinge elements 732a', 732b', 732c'. The edges of the struts and hinge elements are illustrated as solid lines.

A difference from the embodiment of FIG. 12 is that in FIG. 13 the U-shaped hinge elements 732a' are tangent to the linear ring struts 730'. The tangent relationship is evident from the absence of interior spaces between reference lines 800' and the edges of the U-shaped hinge elements 732a'. The reference lines 800' coincide with and extend out from the edges of the linear ring struts 730'. Notice that the edges of the U-shaped hinge elements 732a' do not cross over the reference lines 800', so that an interior space (similar to space 800 in FIG. 12) is not formed. In addition, the bend radii of the tangent U-shaped hinge elements 732a' of FIG. 13 are smaller than those for the non-tangent hinge elements 732a of FIG. 12. Further, the overall length of linear ring struts 730' is longer in FIG. 13 than linear ring struts 730 in FIG. 12. The combination of these features makes the U-shaped hinge elements 732a' of FIG. 13 have less material than those in FIG. 12. The decrease in material is evident from the fact that the length of the inside curve 808' of the tangent U-shaped hinge element 732a' is less than the inside curve 808 of the non-tangent U-shaped hinge element 732a of FIG. 12. One advantage to having less material inside curve 808' of the tangent U shaped hinge element 732a' is that the elements undergo a lower amount of compressive deformation when crimped, thereby preventing damage. This damage may not be readily apparent immediately after crimping yet lead to strut fractures when the stent is deployed later.

Another difference from FIG. 12 is that for each W-shaped closed cell of the stent pattern, the crests at the U-shaped hinge elements 732a' adjacent a linear link strut 734 are circumferentially offset from each other. The circumferential position of the crests are indicated by dash-dot reference lines, and the circumferential offset distance is indicated by the letter "d".

Referring to FIG. 13, the linear link struts 730' have overall lengths L', which can be measured as the length of one of the straight edges of the strut. Also, the linear ring struts 730' are oriented relative to the linear link struts 734' at the different angles. Each linear link strut 734' is connected to a first ring strut 730' and a second ring strut 730'. The first and second ring struts are connected to opposite ends of the linear link strut. The first ring strut is oriented at an angle J' relative to the link strut. The second ring strut is oriented at an angle K' relative to the link strut. Angle J' is greater than angle K'. Angle J' is less than both angles J and K of FIG. 12. Also, the linear ring struts 730' and the U-shaped hinge elements 732a' have a width 737' that is substantially uniform throughout the linear ring struts and U-shaped hinge elements.

A change in angles J' and K' could affect the mechanical properties of the link struts and hinge elements. This is because blow molding and radial expansion of the stock tube creates a precursor tube with polymer chains having a preferred orientation at the molecular level. Structural elements of the stent which are cut from the precursor tube are expected to be more rigid along the direction of the polymer chain orientation. For example, linear ring struts that are cut at an angle that substantially coincides with the polymer chain orientation may provide greater hoop strength and greater resistance to radial loads after deployment, but may make the stent too stiff in the longitudinal direction after crimping. Longitudinal flexibility is desired to facilitate delivery of a stent through tortuous vasculature of a patient. Linear ring struts that are cut at an angle offset from the polymer chain orientation may be more flexible and better able to withstand mechanical stress from crimping and deployment. Also, the configuration and orientation of hinge elements relative to the polymer chain orientation may affect post-crimp and post-deployment recoil characteristics of the stent.

EXAMPLE 1

Stock tubing made of extruded PLLA was radially expanded in a blow mold to form a precursor tube having an outer diameter of about 2.5 mm (about 0.100 inches). The precursor tube was laser cut to have the stent pattern of FIGS. 4 and 6 except that the U-shaped hinge elements were tangent to the linear ring struts. The resulting stent was then crimped to an outer diameter of 1.3 mm onto a balloon catheter, then deployed by radially expanding to an outer diameter of 3.8 mm.

EXAMPLE 2

Stock tubing made of extruded PLLA was radially expanded in a blow mold to form a precursor tube having an outer diameter of about 2.5 mm. The precursor tube was laser cut to have the stent pattern of FIGS. 4 and 6 with the non-tangent U-shaped hinge elements of FIG. 12 in order to increase the amount of material between the linear ring struts. The resulting stent was then crimped to an outer diameter of 1.3 mm onto a balloon catheter, then deployed by radially expanding to an outer diameter of 3.8 mm. Compared to Example 1, Example 2 exhibited less cracks at bent areas between the linear ring struts as a result of crimping and deployment.

EXAMPLE 3 AND FIGS. 12 & 14

Stock tubing made of extruded PLLA was radially expanded in a blow mold to form a precursor tube having an outer diameter of 3.5 mm. The precursor tube was laser cut to have the stent pattern of FIGS. 4 and 6 with the non-tangent U-shaped hinge elements of FIG. 12. The resulting stent was then crimped to an outer diameter of 1.3 mm onto a balloon catheter, then deployed by radially expanding to an outer diameter of 3.8 mm.

In FIG. 12, the following dimensions apply prior to crimping and deployment. Each of the U-shaped hinge elements and the linear ring struts have both a uniform width of about 0.17 mm±0.04 mm and uniform thickness of about 0.15 mm±0.03 mm. The thickness is the same as the radial thickness of the blow molded precursor tube and can be measured as the difference between the inner and outer diameters of the precursor tube. Each linear ring strut 730 is oriented relative to the linear link struts 734 at an angle (J and K) of approximately 65 degrees. The middle segment 804 of each U-shaped hinge element has an inner edge radius Ri and outer edge radius Ro. The inner edge radius Ri corresponds to the inner edge and is approximately 0.33 mm. The outer edge radius Ro corresponds to the outer edge and is approximately 0.48 mm.

Figure 14:
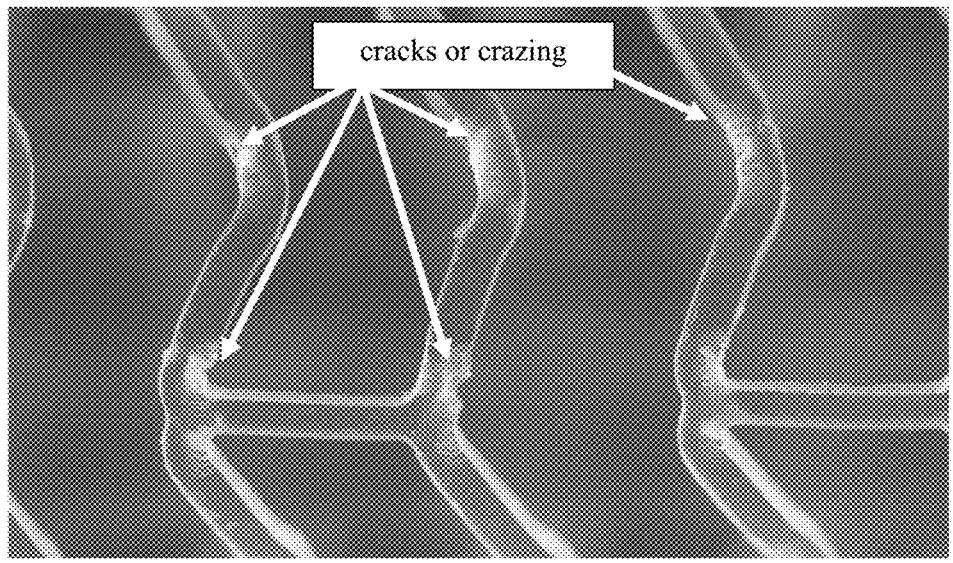
FIG. 14 depicts a photograph of a stent having U-shaped hinge elements that are non-tangent to linear ring struts, showing cracks and crazing at bend areas after crimping and deployment of the stent.

A photograph of the stent after deployment is shown in FIG. 14. The U-shaped and Y-shaped hinge elements have damage clearly visible as crazing and cracks. The visible damage extends at least one third into the width 737 of the U-shaped and Y-shaped hinge elements.

EXAMPLE 4 AND FIGS. 13 & 15

Stock tubing made of extruded PLLA was radially expanded in a blow mold to form a precursor tube having an outer diameter of 3.5 mm, as in Example 3. The precursor tube was laser cut to have the stent pattern of FIGS. 4 and 6 with the tangent U-shaped hinge elements of FIG. 13. The resulting stent was then crimped to an outer diameter of 1.3 mm onto a balloon catheter, then deployed by radially expanding to an outer diameter of 3.8 mm.

In FIG. 13, the following dimensions apply prior to crimping and deployment. Each of the U-shaped hinge elements and the linear ring struts have both a uniform width of about 0.17 mm±0.04 mm and uniform thickness of about 0.15 mm±0.03 mm, which are substantially the same as in Example 3. Each U-shaped hinge element has an inner edge radius Ri' and outer edge radius Ro', which are smaller than corresponding radii in Example 3. The inner edge radius Ri' corresponds to the inner edge and is approximately 0.25 mm. The outer edge radius Ro' corresponds to the outer edge and is approximately 0.41 mm.

The linear ring struts are oriented relative to the linear link struts at different angles. Opposite ends of each linear link strut are respectively connected to a first ring strut and a second ring strut. The first and second ring struts are connected to opposite ends of the linear link strut. The first ring strut is oriented relative to the link strut at an angle (J') of approximately 50 degrees. The second ring strut is oriented relative to the link strut at an angle (K') of approximately 40 degrees. By comparison, angles J and K are approximately 65 degrees for Example 3 (FIG. 12).

Figure 15:
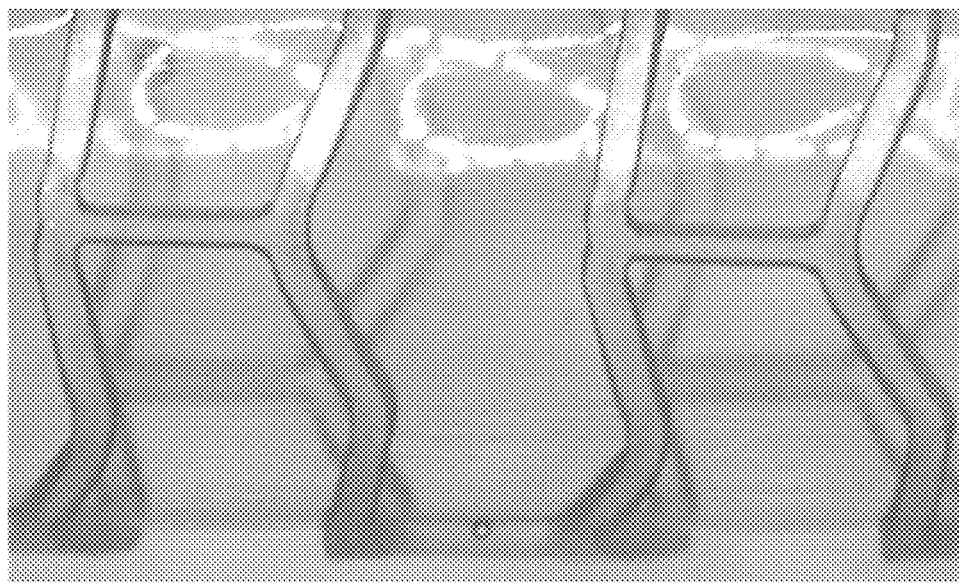
FIG. 15 depicts a photograph of a stent having U-shaped hinge elements that are tangent to linear ring struts, showing an absence of cracks and crazing at bend areas after crimping and deployment of the stent.

A photograph of the stent after deployment is shown in FIG. 15. Compared to Example 3, Example 4 exhibited a significant decrease in crazing and cracks at bent areas between the linear ring struts 730'. No substantial damage was observed on the hinge elements. The improvement in crack resistance was unexpected in that the tangent U-shaped hinge elements provided less material for distributing stresses as compared to non-tangent U-shaped hinge elements of Example 3.

A summary of Examples 1 through 4 is shown in TABLE 1. It is to be understood that the stents for Examples 1 through 4 were made of PLLA and had strut patterns defined by W-shaped closed cells in an offset brick arrangement, with some differences being in the parameters listed in TABLE 1. In Examples 1 through 4, the strut pattern included pairs of rings made up of exactly three W-shaped closed cells arranged circumferentially. The circumferential series of three W-shaped closed cells repeat in the axial direction to form the tubular body of the stent, wherein none of the linear link struts are directly connected to a linear link strut of an axially adjacent cell. Also, all expanded precursor tubes have the same thickness in Examples 1 through 4.

TABLE 1

| Parameter | Example 1 | Example 2 | Example 3 | Example 4 |
|---|---|---|---|---|
| Outer Diameter of Precursor Tube | 2.5 mm | 2.5 mm | 3.5 mm | 3.5 mm |
| Outer Diameter after Crimping | 1.3 mm | 1.3 mm | 1.3 mm | 1.3 mm |
| Outer Diameter after Deployment | 3.8 mm | 3.8 mm | 3.8 mm | 3.8 mm |
| U-shaped Hinge: Tangency | tangent | not tangent | not tangent | tangent |
| U-shaped Hinge: Inner Radius, Ri | | | 33 degrees | 25 degrees |
| U-shaped Hinge: Outer Radius, Ro | | | 48 degrees | 41 degrees |
| Strut Angle | | | J = 65 degrees K = 65 degrees | J' = 50 degrees K' = 40 degrees |
| Comparison | | Less damage than Example 1 | Less post-deployment recoil than Example 2 | Less damage than Example 3 |

Curvilinear Length

Applicants have found that adjustment of another parameter, namely curvilinear length, can be adjusted to increase the resistance of polymeric stents to fracture during deployment by balloons.

Figure 16:
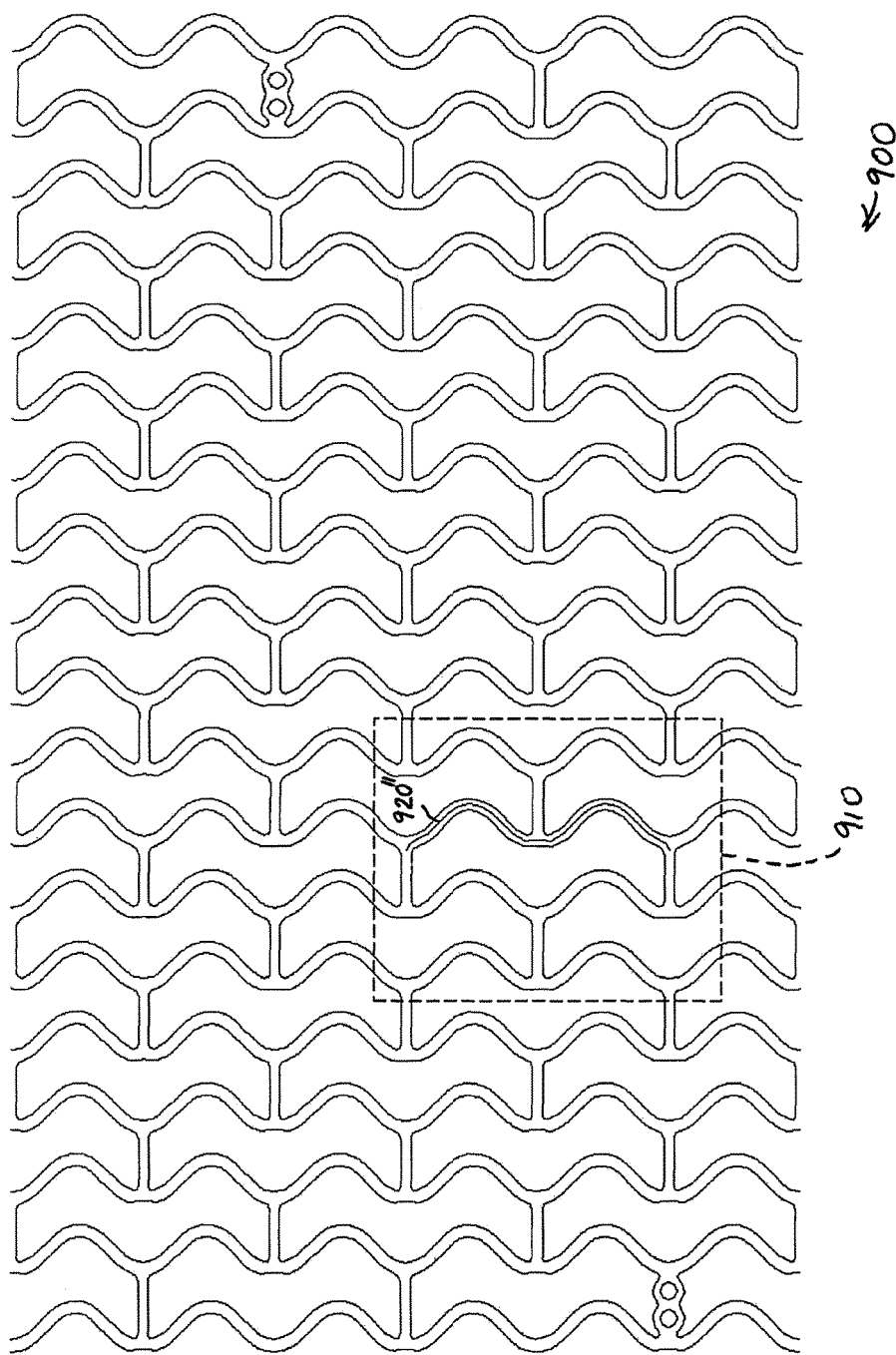
FIG. 16 depicts another stent pattern viewed in a flat or planar state, the pattern having U-shaped hinge elements that are tangent to linear ring struts.

FIG. 16 shows another stent pattern 900 defined by W-shaped closed cells in an offset brick arrangement, with U-shaped hinge elements tangent to adjacent linear ring struts. Test results for the pattern of FIG. 16 will be discussed below in relation to the pattern of FIG. 4 which, as previously discussed, has U-shaped hinge elements that are not tangent to adjacent linear ring struts. It is to be understood that in FIGS. 4 and 16, the top edge of the illustrated pattern wraps around and meets with the bottom edge of the illustrated pattern when used to cut a precursor tube.

Figure 18:
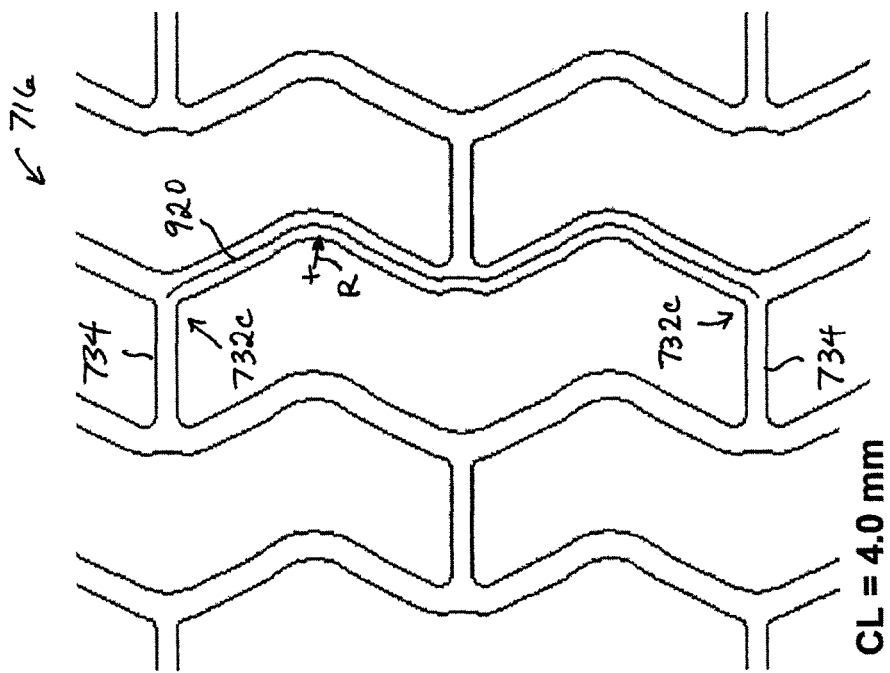
FIG. 18 depicts a detail view of a rectangular region of the pattern of FIG. 4, illustrating, for the purpose of comparison with FIG. 17, the curvilinear length (CL) of one W-shaped closed cell representative of surrounding W-shaped closed cells.
Figure 17:
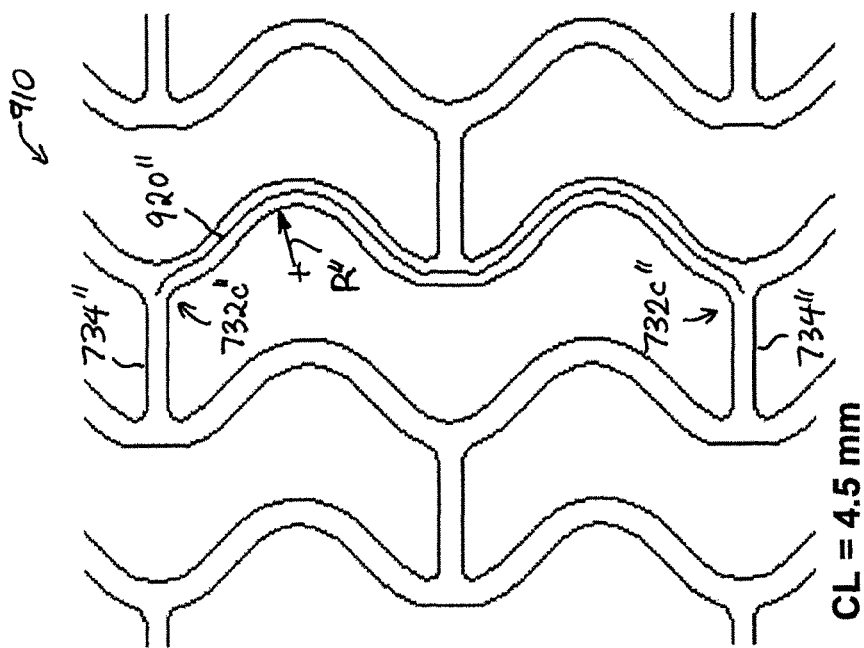
FIG. 17 depicts a detail view of a rectangular region of the pattern of FIG. 16, illustrating the curvilinear length of one W-shaped closed cell representative of surrounding W-shaped closed cells.

In addition to the difference in tangency, the patterns of FIGS. 4 and 16 differ in terms of curvilinear length which defines, in part, the size of the W-shaped closed cells. FIG. 17 shows a detail view of a rectangular region 910 of FIG. 16 bounded by broken lines, and FIG. 18 shows a detailed view within the rectangular region 716 of FIG. 4. The curvilinear length of the W-shaped cell is the length of a curve 920", 920 that runs continuously through the center of the linear ring struts and hinge elements at one side of cell. The curve runs from the Y-shaped hinge element 732c", 732c at the top linear link strut 734", 734 to the Y-shaped hinge element 732c", 732c at the bottom linear link strut 734", 734.

For the baseline pattern of FIGS. 4 and 18, the curvilinear length (i.e., the length of curve 920) is at or about 4.0 mm (0.159 inch). Also, the width of every linear link strut 734 in FIG. 18 is at or about 0.13 mm (0.0050 inch).

For the modified pattern of FIGS. 16 and 17, the curvilinear length (i.e., the length of curve 920") is at or about 4.5 mm (0.175 inch), which is significantly longer than that for the baseline pattern of FIGS. 4 and 18. The increase in curvilinear length of the W-shaped cells was accomplished by increasing crest radii, R", and arc length. The U-shaped hinge elements have a bend radius, R", that is greater than in the baseline pattern. Creating longer arcs is intended to reduce crazing and cracking by reducing stress concentrations during stent crimping and deployment. Also, the width of every linear link strut 734" in FIGS. 16 and 17 is at or about 0.14 mm (0.0055 inch), which is thicker than that for the baseline pattern of FIGS. 4 and 18. The increase in width is intended to reduce risk of linear link strut fractures during bending.

First Comparative Test for Curvilinear Length

Samples of both the baseline pattern (FIGS. 4 and 18) and modified pattern (FIGS. 16 and 17) were tested to compare their resistance to fracture during deployment. The test procedure involved cutting the pattern onto a precursor tube of blow molded PLLA polymer, the tube having an outer diameter of about 3.5 mm (0.1378 inches) and an inner diameter of about 3.2 mm (0.1260 inches). The stents were coated with drug/polymer solution and the solvents in the solution were dried away. The stents were also sterilized. The stent was placed over a balloon catheter, but not crimped in order to examine expansion capability without the effects from crimping. The balloon was inflated by increasing pressure at increments of 1 atmosphere (atm). After initial inflation to 1 atm, the stent on the balloon was inspected for fractures. If no fractures were found, the inner diameter of the stent (outer diameter of the balloon) was determined and recorded. Then inflation pressure was increased to 2 atm (increase of 1 atm), and the stent was inspected again for fractures. If no fractures were found, the inner diameter of the stent (outer diameter of the balloon) was again determined and recorded. This process was repeated until the stent fractured.

The modified pattern of FIGS. 16 and 17 (having a longer curvilinear length than the baseline pattern) exhibited greater resistance to fracture from overexpansion. On average, stents having the modified pattern with the longer curvilinear length (CL=4.5 mm) were expanded to an inner diameter of 4.48 mm before fracture occurred, as compared to 3.84 mm for the baseline pattern (FIGS. 4 and 18) with the shorter curvilinear length (CL=4.0 mm).

Second Comparative Test for Curvilinear Length

Samples of both the baseline pattern (FIGS. 4 and 18) and modified pattern (FIGS. 16 and 17) were tested in the same manner as in the First Comparative Test, except the stents were crimped onto the balloon prior to expansion by the balloon.

The modified pattern of FIGS. 16 and 17 (having a longer curvilinear length than the baseline pattern) exhibited greater resistance to fracture from overexpansion. On average, stents having the modified pattern with the longer curvilinear length (4.5 mm) were expanded to an inner diameter of 4.54 mm before fracture occurred, as compared to 3.83 mm for the baseline pattern with the shorter curvilinear length (4.0 mm).

A summary of the first and second comparative tests is shown in TABLE 2. It is to be understood that the samples for the both tests used stents configured to be crimped to an outer diameter of about 1.3 mm and expanded to an outer diameter of about 3.8 mm. The stents were made of a PLLA precursor tube cut with strut patterns defined by W-shaped closed cells in an offset brick arrangement, as generally shown in FIGS. 4 and 16. In both comparative tests, with and without crimping prior to deployment, the stent having greater CL was capable of being expanded to a greater diameter during deployment than the stent with smaller CL.

TABLE 2

| | CL = 4.0 mm (Baseline Pattern, FIGS. 4 & 18) | | CL = 4.5 mm (Modified Pattern, FIGS. 16 & 17) | |
|---|---|---|---|---|
| | Not Crimped prior to Deployment | Crimped prior to Deployment | Not Crimped prior to Deployment | Crimped prior to Deployment |
| Inner Diameter of Stent at 1 atm Before Fracture | 3.84 mm | 3.83 mm | 4.48 mm | 4.54 mm |

Figure 19B:
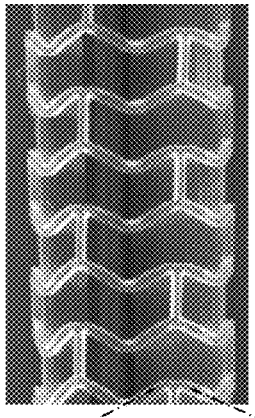
FIGS. 19A and 19B are photographs of a stent in a crimped and expanded state, the stent having a pattern of W-shaped closed cell with CL=4.0 mm.
Figure 19A:

In some uses, stents having the baseline and modified patterns are expanded during deployment to an inner diameter of about 3.5 mm. FIGS. 19A and 19B show a stent with the baseline pattern (CL=4.0 mm, FIGS. 4 and 18) in crimped and deployed states, respectively. FIG. 19B shows that when the stent is deployed at 3.5 mm, the linear ring struts form interior angles θ1 between each other. The interior angle is significant in that, if the angle is significantly decreased due to a design modification, there is an increased risk that the stent will recoil after deployment due to a tendency for the linear ring struts collapse back toward each other (i.e., the bending elements will tend to return to the state that they were in after crimping).

Figure 20B:
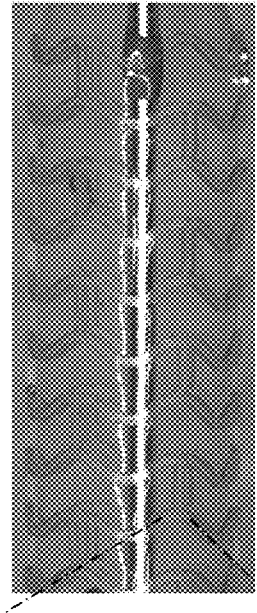
FIGS. 20A and 20B are photographs of a stent in a crimped and expanded state, the stent having a pattern of W-shaped closed cell with CL=4.5 mm.
Figure 20A:
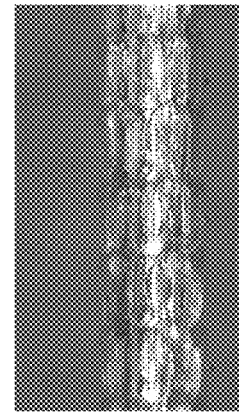

FIGS. 20A and 20B show a stent with the modified pattern (CL=4.5 mm, FIGS. 16 and 17) in crimped and deployed states, respectively. FIG. 20B shows that when the stent is deployed at 3.5 mm, the linear ring struts form interior angles θ2 between each other. As can be seen from the figures, the interior angle θ2 for the modified pattern appears substantially similar in size to the interior angle θ1 for the baseline pattern, with little noticeable decrease in interior angle. The similarity of the interior angles indicates that even through the curvilinear length was increased (to allow for significant fracture resistance from overexpansion), the risk of post-deployment recoil was not likely increased significantly.

Figure 21B:
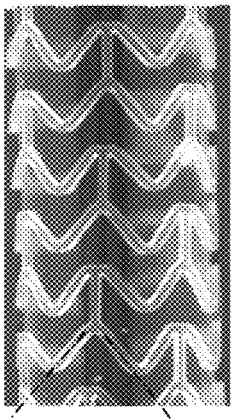
FIGS. 21A and 21B are photographs of a stent in a crimped and expanded state, the stent having a pattern of W-shaped closed cell with CL>4.5 mm.
Figure 21A:
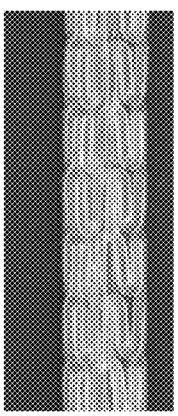

FIGS. 21A and 21B show a stent with a further modified pattern having CL=5.0 mm in crimped and deployed states, respectively. The "further modified" pattern is similar to the baseline pattern, except that the length of the linear ring struts were increased so that the curvilinear length (CL) for the W-shaped cells are longer than that for the baseline (CL=4.0 mm) and modified patterns (CL=4.5 mm). FIG. 21B shows that when the stent is deployed at 3.5 mm, the linear ring struts form interior angles θ3 between each other. As can be seen from the figures, the interior angle θ3 for the CL=5.0 mm is markedly smaller than the interior angle θ1 for CL=4.0 mm and the interior angle θ2 for CL=4.5 mm. The decrease in interior angle is due to the increase in curvilinear length and indicates that the risk of post-deployment recoil could increase. Therefore, it will be appreciated that CL should be carefully selected to be within a range that will increase fracture resistance during deployment without unduly increasing the potential for post-deployment recoil.

In some embodiments, a stent having a substrate made entirely of PLLA and configured to be crimped to an outer diameter of about 1.3 mm and expanded to an outer diameter of at least 3.5 mm and more narrowly to about 3.8 mm, has a strut pattern of W-shaped closed cells in an offset brick arrangement with a curvilinear length (CL) that is greater than about 4.0 mm and less than about 5.0 mm, and more narrowly at or about 4.5 mm. The phrase "substrate" refers to the material at the core of the structural element of the stent scaffold and does not include any coatings of other material deposited after formation of the stent scaffold. The substrate can be formed from an extruded PLLA tube having 0.64 mm (0.025 inch) ID and 1.7 mm (0.066 inch) OD, which is then radially expanded by blow molding to an outer diameter of 3.5 mm to make a precursor tube out of which the scaffold pattern is cut. In further embodiments, the stent can have a coating over the substrate. The coating can contain any one of a mixture of the polymers, therapeutic agents, solvents and other substances described above. In further embodiments, the scaffold of the stent includes a plurality of undulating rings formed linear ring struts and U-shaped hinge elements. The rings are arranged axially to form the tubular scaffold. For each pair of rings, one ring is connected to a second ring by exactly three linear link struts oriented axially so as to form exactly three W-shaped closed cells arranged circumferentially. Each of the W-shaped closed cells having a curvilinear length (CL) that is greater than about 4.0 mm and less than about 5.0 mm, and more narrowly at or about 4.5 mm. Since each ring corresponds to exactly three W-shaped closed cells arranged circumferentially, each ring can have an overall curvilinear length that is about 12.0 mm to about 15.0 mm, and more narrowly at or about 13.5 mm. The overall curvilinear length of the ring is the sum of curvilinear lengths of the three W-shaped closed cells.

While several particular forms of the invention have been illustrated and described, it will also be apparent that various modifications can be made without departing from the scope of the invention. It is also contemplated that various combinations or subcombinations of the specific features and aspects of the disclosed embodiments can be combined with or substituted for one another in order to form varying modes of the invention. Accordingly, it is not intended that the invention be limited, except as by the appended claims.

What is claimed is:

1. An endoprosthesis comprising:
   a tubular network of struts cut from a radially expanded polymer tube, the tubular network having a central axis and comprising W-shaped closed cells, each W-shaped closed cell abutting six other W-shaped closed cells, each W-shaped closed cell comprising ring struts, link struts, U-shaped hinge elements, and Y-shaped hinge elements, the ring struts forming a plurality of ring structures, each ring structure connected to another one of the ring structures by at least one link strut, each U-shaped hinge element connecting exactly two ring struts to each other, the U-shaped hinge element being tangent to the two ring struts, each Y-shaped hinge element connecting a link strut to exactly two ring struts,
   wherein each ring structure has an overall curvilinear length from about 12 mm to about 15 mm, an interior space of each of the W-shaped closed cells has an axial dimension that is parallel to the central axis, and the axial dimension is substantially constant with respect to circumferential position within the W-shaped closed cell, and
   wherein the radially expanded polymer tube, from which the tubular network of struts are cut, forms a polymer core of the ring struts,
   wherein each ring structure is connected to an adjacent ring structure by exactly three of the link struts so as to form a ring structure pair, there being a plurality of ring structure pairs and there being exactly three W-shaped closed cells within each of the ring structure pairs,
   wherein the tubular network has an pre-crimp outer diameter and is configured to be crimped from the pre-crimp outer diameter to a post-crimp outer diameter that is less than the pre-crimp outer diameter, and
   when the tubular network is at the pre-crimp outer diameter, one of the link struts is connected to a first ring strut and a second ring strut, the first and second ring struts connected to opposite ends of the link strut, the first ring strut oriented at about 40 degrees relative to the link strut, the second ring strut oriented at about 50 degrees relative to the link strut.

2. The endoprosthesis of claim 1, wherein the pre-crimp outer diameter is about 3.5 mm, the post-crimp outer diameter is about 1.3 mm, and the tubular network is configured to be expanded from the post-crimp diameter to an expanded outer diameter of about 3.8 mm.

3. The endoprosthesis of claim 2, wherein the first ring strut is connected to a first U-shaped hinge element and the second ring strut is connected to a second U-shaped hinge element circumferentially offset from the first U-shaped hinge element when the tubular network is at the post-crimp outer diameter.

4. The endoprosthesis of claim 1, wherein each W-shaped closed cell has a perimeter that includes eight of the ring struts and two of the link struts.

5. The endoprosthesis of claim 1, wherein each W-shaped closed cell has a perimeter that includes four of the U-shaped hinge elements and six of the Y-shaped hinge elements.

6. The endoprosthesis of claim 1, wherein each of the W-shaped closed cells within each ring structure pair has a curvilinear length from about 4 mm to about 5 mm.

7. The endoprosthesis of claim 6, wherein each of the W-shaped closed cells within each ring structure pair has a curvilinear length of about 4.5 mm.

8. The endoprosthesis of claim 1, wherein each ring structure has an overall curvilinear length of about 13.5 mm.

9. An endoprosthesis comprising:
   a tubular network of struts cut from a radially expanded polymer tube, the tubular network having a central axis and comprising W-shaped closed cells, each W-shaped closed cell abutting six other W-shaped closed cells, each W-shaped closed cell comprising ring struts, link struts, U-shaped hinge elements, and Y-shaped hinge elements, the ring struts forming a plurality of ring structures, each ring structure connected to another one of the ring structures by at least one link strut, each U-shaped hinge element connecting exactly two ring struts to each other, the U-shaped hinge element being tangent to the two ring struts, each Y-shaped hinge element connecting a link strut to exactly two ring struts,
   wherein each ring structure has an overall curvilinear length from about 12 mm to about 15 mm, an interior space of each of the W-shaped closed cells has an axial dimension that is parallel to the central axis, and the axial dimension is substantially constant with respect to circumferential position within the W-shaped closed cell, and wherein the radially expanded polymer tube, from which the tubular network of struts are cut, forms a polymer core of the ring struts, wherein each ring structure is connected to an adjacent ring structure by exactly three of the link struts so as to form a ring structure pair, there being a plurality of ring structure pairs and there being exactly three W-shaped closed cells within each of the ring structure pairs, wherein the tubular network has a pre-crimp outer diameter and is configured to be crimped from the pre-crimp outer diameter to a post-crimp outer diameter that is less than the pre-crimp outer diameter, and wherein one of the link struts is connected to a first ring strut and a second ring strut, the first and second ring struts connected to opposite ends of the link strut, the first ring strut is connected to a first U-shaped hinge element and the second ring strut is connected to a second U-shaped hinge element circumferentially offset from the first U-shaped hinge element when the tubular network is at the pre-crimp outer diameter.

10. The endoprosthesis of claim 9, wherein the pre-crimp outer diameter is about 3.5 mm, the post-crimp outer diameter is about 1.3 mm, and the tubular network is configured to be expanded from the post-crimp diameter to an expanded outer diameter of about 3.8 mm.

\* \* \* \* \*